United States Patent
Kawatsu

[11] Patent Number: 5,897,766
[45] Date of Patent: Apr. 27, 1999

[54] APPARATUS FOR DETECTING CARBON MONOXIDE, ORGANIC COMPOUND, AND LOWER ALCOHOL

[75] Inventor: Shigeyuki Kawatsu, Susono, Japan

[73] Assignee: Toyota Jidosa Kabushiki Kaisha, Toyota, Japan

[21] Appl. No.: 08/552,207

[22] Filed: Nov. 2, 1995

[30] Foreign Application Priority Data

| Nov. 2, 1994 | [JP] | Japan | 6-293808 |
| Mar. 31, 1995 | [JP] | Japan | 7-100313 |
| Sep. 22, 1995 | [JP] | Japan | 7-269244 |

[51] Int. Cl.⁶ .................................. G01N 27/407
[52] U.S. Cl. .............. 204/426; 204/409; 204/424; 204/427; 205/784; 205/787; 429/30
[58] Field of Search .................. 204/400, 421–429, 204/431, 432, 406, 409

[56] References Cited

U.S. PATENT DOCUMENTS

| 2,913,511 | 11/1959 | Grubb | 429/30 |
| 3,216,911 | 11/1965 | Kronenberg | 204/412 |
| 3,342,558 | 9/1967 | Reinecke | 204/424 |
| 3,432,404 | 3/1969 | Erdos et al. | 204/431 |
| 3,597,345 | 8/1971 | Hickam et al. | 204/427 |
| 3,773,136 | 11/1973 | Palazzetti et al. | 180/168 |
| 4,024,036 | 5/1977 | Nakamura et al. | 204/427 |
| 4,105,524 | 8/1978 | Fujishiro et al. | 204/427 |
| 4,127,462 | 11/1978 | Blurton | 204/432 |
| 4,171,253 | 10/1979 | Nolan et al. | 204/411 |
| 4,227,984 | 10/1980 | Dempsey et al. | 204/424 |
| 4,452,682 | 6/1984 | Takata et al. | 204/416 |
| 4,525,266 | 6/1985 | Schmidt et al. | 204/431 |
| 4,581,121 | 4/1986 | Dailey et al. | 254/406 |
| 5,164,053 | 11/1992 | Razaq et al. | 204/424 |
| 5,302,274 | 4/1994 | Tomantschger et al. | 204/427 |

FOREIGN PATENT DOCUMENTS

| 53-115293 | 10/1978 | Japan . |
| 3-211454 | 9/1991 | Japan . |
| 3-74468 | 11/1991 | Japan . |

*Primary Examiner*—T. Tung
*Attorney, Agent, or Firm*—Oblon, Spivak, McClelland, Maier & Neustadt, P. C.

[57] ABSTRACT

An apparatus or method of the present invention measures carbon monoxide included in a hydrogen-rich reactant gas with high precision, and also measures a lower alcohol or another organic compound included in the reactant gas. A carbon monoxide sensor (1) includes an electrolyte membrane (10), a pair of electrodes (12,14) arranged across the electrolyte membrane (10) to form a sandwich structure, a pair of holders (20,22) for supporting the sandwich structure as well as pair of metal plates (16,18), and an insulating member 24 for connecting the holders (20,22) with each other. A gas flow conduit (28) is joined with one holder (20), and a gaseous fuel is fed to the electrode (12) via the gas flow conduit (28). The electrode (14) supported by the other holder (22) is exposed to the atmosphere. A resistor (34) is connected to detection terminals (20T,22T) of the holders (20,22), and a potential difference between both terminals of the resistor (34) is measured with a voltmeter (32). The voltmeter (32) outputs a signal representing the measured potential difference to an external control system. The control system determines the degree of poisoning and the concentration of carbon monoxide, based on the signal representing the measured potential difference.

7 Claims, 19 Drawing Sheets

APPARATUS FOR DETECTING CARBON MONOXIDE, ORGANIC COMPOUND, AND LOWER ALCOHOL

BACKGROUND OF THE INVENTION

1. Field of the Invention

The present invention relates to an apparatus for detecting carbon monoxide included in a hydrogen-containing reactant gas, an apparatus for detecting an organic compound included in the reactant gas, and an apparatus for detecting a lower alcohol included in the reactant gas. The present invention also pertains to the respective methods of detecting carbon monoxide, an organic compound, and a lower alcohol.

2. Description of the Related Art

Fuel cells are known apparatus in which the chemical energy of a fuel is converted directly into electrical energy. The fuel cell generally has a pair of electrodes arranged across an electrolyte, where the surface of one electrode is exposed to reactive gaseous hydrogen or gaseous fuel while the surface of the other electrode being exposed to an oxidizing gas containing oxygen. The electrical energy is generated between the electrodes through the electrochemical reactions occurring by the exposure.

A gaseous fuel supplied to such fuel cells is generated by a reformer, where methanol is steam-reformed according to the following reactions:

$$CH_3OH \rightarrow CO + 2H_2 - 21.7 \text{ kcal/mol (endothermic reaction)} \quad (1)$$

$$CO + H_2O \rightarrow CO_2 + H_2 + 9.8 \text{ kcal/mol (exothermic reaction)} \quad (2)$$

$$CH_3OH + H_2O \rightarrow CO_2 + 3H_2 - 11.9 \text{ kcal/mol (endothermic reaction)} \quad (3)$$

Carbon monoxide (CO) generated through the reaction expressed by Equation (1) is converted to carbon dioxide (CO2) by the reaction of Equation (2), and thus does not participate in the reforming reaction expressed by Equation (3). The rate of reaction expressed by Equation (1) may be different from the rate of reaction expressed by Equation (2), depending upon the reaction conditions, such as temperature and pressure. Carbon monoxide (CO) generated in the reaction of Equation (1) thus remains and is adsorbed by platinum catalyst or platinum-containing alloy catalyst on the fuel electrode and interferes with the catalytic action of platinum. This is generally referred to as poisoning of catalyst. Generators utilizing such fuel cells accordingly require a structure allowing the presence of carbon monoxide in the gaseous fuel fed from the reformer.

A variety of carbon monoxide sensors have been developed for determining the concentration of carbon monoxide included in a supply of gaseous fuel fed to the fuel cells.

A typical example is a potentiostatic electrolysis-based carbon monoxide sensor, which utilizes potentiostatic electrolysis applied to electrochemical analysis in solutions. FIG. 21 schematically illustrates a conventional potentiostatic electrolysis-based carbon monoxide sensor, which includes three electrodes; that is, a reference electrode P1, a counter electrode P2, and a working electrode P3.

These electrodes P1, P2, and P3 are exposed to a phase of electrolytic solution and a gas phase. When carbon monoxide comes into contact with the working electrode P3, an anode reaction shown below proceeds:

$$CO + H_2O \rightarrow CO_2 + 2H^+ + 2e^-$$

while a cathode reaction shown below proceeds on the counter electrode P2 exposed to oxygen included in the air:

$$(\tfrac{1}{2})O_2 + 2H^+ + 2e^- \rightarrow H_2O$$

The total reaction is accordingly expressed by:

$$CO + (\tfrac{1}{2})O_2 \rightarrow CO_2$$

The concentration of carbon monoxide is then determined by measuring the electric current generated through the oxidation of carbon monoxide with an ammeter P4.

This conventional carbon monoxide sensor can determine the concentration of carbon monoxide included in the air with high precision, but is significantly affected by the presence of hydrogen because of its principles of measurement. The conventional potentiostatic electrolysis-based sensor is thus not suitable for determining the concentration of carbon monoxide included in the hydrogen-rich gaseous fuel, which contains only a trace amount of carbon monoxide in an extremely large amount of hydrogen. The sensor naturally has a low sensitivity of detection to hydrogen, which is approximately 1/80 that to carbon monoxide. Since a supply of gaseous fuel fed to fuel cells contains an extremely large amount of hydrogen, the sensor simultaneously detects hydrogen and carbon monoxide and suffers from a problem of low precision in the measurement of carbon monoxide.

Like the potentiostatic electrolysis-based sensor described above, another known carbon monoxide sensor based on catalytic combustion has been developed originally for measuring carbon monoxide included in the air. The problem of poor precision thus arises in the process of measuring carbon monoxide included in the hydrogen-rich gaseous fuel.

Apparatus for detecting organic compounds and those for detecting lower alcohols have also been proposed and utilized.

Known methanol-detecting apparatus, which correspond to both the organic compound-detecting apparatus and the lower alcohol-detecting apparatus, are used for detecting methanol included in gasoline (for example, JAPANESE PATENT PUBLICATION GAZETTE No. H-3-48533). Such an apparatus is constructed as a cell including an ion-exchange membrane and two electrodes arranged across the ion-exchange membrane, where gasoline is fed to one electrode and an electrolytic solution, that is, 10 percent by weight of aqueous sulfuric acid, to the other electrode. On the electrode exposed to gasoline, a reaction expressed by Equation (4) below proceeds to generate carbon dioxide, hydrogen ions and electrons from methanol and water included in gasoline. On the electrode exposed to the electrolytic solution, a reaction expressed by Equation (5) below proceeds to generate water from hydrogen ions permeated through the ion-exchange membrane and oxygen and electrons included in the electrolytic solution.

$$CH_3OH + H_2O \rightarrow CO_2 + 6H^+ + 6e^- \quad (4)$$

$$(\tfrac{3}{2})O_2 + 6H^+ + 6e^- \rightarrow 3H_2O \quad (5)$$

Electromotive force generated between the electrodes by these electrochemical reactions increases with an increase in concentration of methanol included in gasoline. This apparatus accordingly determines the concentration of methanol included in gasoline, based on the electromotive force generated between the electrodes.

These conventional methanol-detecting apparatus, which are used for detecting methanol included in gasoline, that is, a liquid, can not measure methanol included in a gas, especially, a hydrogen-rich gas. Precise measurement of methanol included in a hydrogen-rich gas leads to efficient operation of methanol reformers for generating a hydrogen-rich gas through the reaction of methanol with water or to efficient operation of fuel cells or other mechanisms for generating electrical energy using as a fuel the hydrogen-rich gas generated by the methanol reformer.

This problem is not characteristic of the methanol-detecting apparatus, but similar problems are also found in apparatus for detecting lower alcohols other than methanol or those for detecting other organic compounds, when petroleum, instead of methanol, is used as material of the reformer.

SUMMARY OF THE INVENTION

One object of the present invention is thus to provide an apparatus for detecting carbon monoxide included in a hydrogen-rich reactant gas with high precision.

Another object of the invention is to provide an apparatus for detecting an organic compound included in the hydrogen-rich reactant gas.

Still another object of the invention is to provide an apparatus for detecting a lower alcohol included in the hydrogen-rich reactant gas.

The above and the other related objects are realized by an apparatus for detecting carbon monoxide included in a hydrogen-containing reactant gas. The carbon monoxide-detecting apparatus comprises: an electrolyte membrane; first and second electrodes with a catalyst carried thereon, the first and the second electrodes being arranged across the electrolyte membrane; a reactant gas supply conduit for supplying the reactant gas to the first electrode; an oxygen gas supply conduit for supplying an oxygen-containing gas to the second electrode; and potential difference measurement means for measuring a potential difference between the first and the second electrodes while a predetermined load is connected to the first and the second electrodes.

The carbon monoxide-detecting apparatus of this structure takes advantage of the principle of fuel cells, that is, conversion of chemical energy to electrical energy. A supply of reactant gas is fed to the first electrode via the reactant gas supply conduit, whereas a supply of oxygen-containing gas is fed to the second electrode via the oxygen gas supply conduit. The chemical energy of the reactant gas is converted to electrical energy by electrochemical reactions, and an electromotive force or potential difference is generated between the first and the second electrodes across the electrolyte membrane. In the carbon monoxide-detecting apparatus of the invention, a predetermined load is connected to the first and the second electrodes so as to make the electrochemical reactions continuously proceed. The potential difference measurement means then measures the potential difference between the two electrodes. Like the known fuel cells, the potential difference measured by the invention lowers by poisoning of the catalyst with carbon monoxide. The potential difference measured accordingly represents the degree of catalyst poisoning and thereby the concentration of carbon monoxide.

The measurement of carbon monoxide by this principle is not affected by the presence of hydrogen. The apparatus of the invention can accordingly determine, with high precision, the concentration of carbon monoxide included in a hydrogen-rich gas containing only a trace amount of carbon monoxide in an extremely large amount of hydrogen, like a gaseous fuel fed to the fuel cells.

According to a preferable structure, the oxygen gas supply conduit comprises an air opening for exposing the second electrode to the atmosphere.

In this structure, the second electrode is exposed to the atmosphere via the air opening and accordingly does not require any specific oxygen gas supply conduit, which effectively reduces the size of the whole carbon monoxide-detecting apparatus. The significantly weak electric current flowing between the electrodes does not require continuous supplies of oxygen-containing gas to the second electrode, but exposure to the atmosphere is sufficient for the purpose.

In accordance with another aspect of the invention, the carbon monoxide-detecting apparatus further comprises: a connection passage for connecting the reactant gas supply conduit to the atmosphere; and valve means disposed in the connection passage, the valve means being driven to an open position when a pressure in the reactant gas supply conduit becomes greater than a predetermined level.

In this structure, the valve means disposed in the connection passage is open when the pressure in the reactant gas supply conduit exceeds a predetermined level, and allows the reactant gas supply conduit to connect with the atmosphere via the connection passage. The high-pressure gas is accordingly released to the atmosphere via the connecting passage. This structure effectively prevents the gas pressure from being abnormally heightened in the reactant gas supply conduit.

It is further preferable that the carbon monoxide-detecting apparatus of this structure comprises valve state detection means for detecting the valve means in its open position.

In this preferable structure, the valve state detection means detects that the valve means is in the open position and informs the user of the above operation for releasing the high-pressure of reactant gas to the atmosphere. This allows a quick response to the abnormal increase of the gas pressure.

It is also preferable that the carbon monoxide-detecting apparatus further comprises temperature control means for controlling temperature of the first electrode.

The temperature control means controls the temperature of the first electrode receiving a supply of reactant gas, thereby adjusting the sensitivity of detection of carbon monoxide. Because of its characteristics, the carbon monoxide-detecting apparatus of the invention is generally applicable for measuring only a restricted range of concentration of carbon monoxide. The temperature control procedure, however, enhances the resistance to catalyst poisoning, and thereby allows the detectable range of carbon monoxide concentration to be varied.

According to another preferable structure, the carbon monoxide-detecting apparatus further comprises means for heating the first electrode to remove carbon monoxide adsorbed by the catalyst on the first electrode.

This structure releases carbon monoxide adsorbed by the catalyst on the first electrode exposed to the reactant gas to be favorably released by heating the first electrode. The catalyst on the electrode surface exposed to the reactant gas generally lowers its catalytic activities by the effect of carbon monoxide of unexpectedly high concentration. The lowered catalytic activities undesirably deteriorate the function of the carbon monoxide-detecting apparatus. The means of this structure, however, increases the temperature of the first electrode to higher and makes carbon monoxide released from the catalyst on the first electrode, thus recovering the catalytic activities and preventing deterioration of the function of the carbon monoxide-detecting apparatus.

The carbon monoxide-detecting apparatus is preferably provided with concentration calculating means for calculating a concentration of carbon monoxide included in the reactant gas, based on the potential difference measured by the potential difference measurement means.

In this structure, the concentration calculating means efficiently calculates the concentration of carbon monoxide included in the reactant gas, based on the potential difference measured by the potential difference measurement means.

In accordance with another aspect of the invention, the carbon monoxide-detecting apparatus further comprises determination means for determining that carbon monoxide of not less than a predetermined concentration exists in the reactant gas when the potential difference measured by the potential difference measurement means is not greater than a preset value.

In this structure, the determination means effectively determines that carbon monoxide existing in the reactant gas exceeds a predetermined concentration when the potential difference measured by the potential difference measurement means is below a preset value.

The invention is also directed to an apparatus for detecting an organic compound included in a hydrogen-containing reactant gas. The organic compound-detecting apparatus comprises: an electrolyte membrane; first and second electrodes with a catalyst carried thereon, the first and the second electrodes being arranged across the electrolyte membrane; a reactant gas supply conduit for supplying the reactant gas to the first electrode; an oxygen gas supply conduit for supplying an oxygen-containing gas to the second electrode; and potential difference measurement means for measuring a potential difference between the first and the second electrodes.

In the organic compound-detecting apparatus of this structure, a supply of reactant gas is fed to the first electrode via the reactant gas supply conduit, whereas a supply of oxygen-containing gas is fed to the second electrode via the oxygen gas supply conduit. The potential difference measurement means then measures a potential difference generated between the first and the second electrodes across the electrolyte membrane. Since the existence of organic compound in the reactant gas decreases the potential difference between the two electrodes, measurement of the potential difference gives the concentration of organic compound included in the reactant gas. The organic compound-detecting apparatus of the invention can accordingly determine the concentration of organic compound included in a hydrogen-rich gas containing only a trace amount of organic compound in an extremely large amount of hydrogen, like a gaseous fuel fed to the fuel cells.

It is preferable that the oxygen gas supply conduit of this organic compound-detecting apparatus further comprises an air opening for exposing the second electrode to the atmosphere.

In this structure, the second electrode is exposed to the atmosphere via the air opening and accordingly does not require any specific oxygen gas supply conduit, which effectively reduces the size of the whole organic compound-detecting apparatus. The significantly weak electric current flowing between the electrodes does not require continuous supplies of oxygen-containing gas to the second electrode, but exposure to the atmosphere is sufficient for the purpose.

According to a preferable application, the organic compound-detecting apparatus further comprises: a connection passage for connecting the reactant gas supply conduit to the atmosphere; and valve means disposed in the connection passage, the valve means being driven to an open position when a pressure in the reactant gas supply conduit becomes greater than a predetermined level.

In this structure, the valve means disposed in the connection passage is open when the pressure in the reactant gas supply conduit exceeds a predetermined level, and allows the reactant gas supply conduit to connect with the atmosphere via the connection passage. The high-pressure gas is accordingly released to the atmosphere via the connecting passage. This structure effectively prevents the gas pressure from being abnormally heightened in the reactant gas supply conduit.

In this structure, the organic compound-detecting apparatus is preferably provided with valve state detection means for detecting the valve means in its open position.

In this preferable structure, the valve state detection means detects that the valve means is in the open position and informs the user of the above operation for releasing the high-pressure of reactant gas to the atmosphere. This allows a quick response to the abnormal increase of the gas pressure.

It is preferable that the organic compound-detecting apparatus further comprises temperature control means for controlling temperature of the first electrode.

The temperature control means controls the temperature of the first electrode receiving a supply of reactant gas, thereby adjusting the sensitivity of detection of organic compound. The temperature control procedure allows the temperature of the first electrode to be set at a desirable level realizing high sensitivity of detection, thereby enhancing the precision of measurement.

In accordance with one aspect of the invention, the organic compound-detecting apparatus further comprises: switching means for moving between a first position where a predetermined load is connected to the first and the second electrodes and a second position where the predetermined load is disconnected from the first and the second electrodes; means for calculating a concentration of carbon monoxide included in the reactant gas, based on the potential difference measured by the potential difference measurement means, while the switching means is in the first position; and means for calculating a concentration of the organic compound included in the reactant gas, based on the potential difference measured by the potential difference measurement means while the switching means is in the second position.

In this structure, the switching means selects either the first position where a predetermined load is connected to the first and the second electrodes or the second position where the predetermined load is disconnected from the two electrodes. The concentration of carbon monoxide-calculating means calculates the concentration of carbon monoxide included in the reactant gas, based on the potential difference measured by the potential difference measurement means, while the switching means selects the first position. The concentration of organic compound-calculating means calculates the concentration of organic compound included in the reactant gas, based on the potential difference measured by the potential difference measurement means, while the switching means selects the second position. The apparatus of this structure can determine both the concentration of carbon monoxide and the concentration of organic compound included in the hydrogen-rich reactant gas by switching between the connection of the predetermined load to the two electrodes and the disconnection of the predetermined load with the two electrodes.

According to another aspect of the invention, the organic compound-detecting apparatus comprises means for calculating a concentration of the organic compound included in the reactant gas, based on the potential difference measured by the potential difference measurement means.

In this structure, the means efficiently calculates the concentration of organic compound included in the reactant gas, based on the potential difference measured by the potential difference measurement means.

In one preferable application, the organic compound-detecting apparatus further comprises determination means for determining that the organic compound of not less than a predetermined concentration exists in the reactant gas when the potential difference measured by the potential difference measurement means is not greater than a preset value.

In this structure, the determination means effectively determines that the organic compound existing in the reactant gas exceeds a predetermined concentration when the potential difference measured by the potential difference measurement means is below a preset value.

The invention is also directed to an apparatus for measuring an organic compound included in a hydrogen-containing reactant gas. The organic compound-detecting apparatus comprises: a multi-layered structure comprising a plurality of layer units laid one upon another, each the layer unit comprising an electrolyte membrane and first and second electrodes having a catalyst carried thereon and arranged across the electrolyte membrane; a reactant gas supply conduit for supplying the reactant gas to the first electrode in the each layer unit of the multi-layered structure; an oxygen gas supply conduit for supplying an oxygen-containing gas to the second electrode in the each layer unit of the multi-layered structure; and potential difference measurement means for measuring a potential difference between the first electrode proximate to a first end of the multi-layered structure and the second electrode proximate to a second end of the multi-layered structure, which is opposite to the first end.

In the organic compound-detecting apparatus of this structure, a supply of reactant gas is fed to the first electrode in each the layer unit of the multi-layered structure via the reactant gas supply conduit, whereas a supply of oxygen-containing gas is fed to the second electrode in each layer unit of the multi-layered structure via the oxygen gas supply conduit. The potential difference measurement means then measures a potential difference generated between the first electrode proximate to a first end of the multi-layered structure and the second electrode proximate to a second end of the multi-layered structure. The organic compound-detecting apparatus of the invention accordingly determines the concentration of organic compound included in the hydrogen-rich reactant gas.

In accordance with a preferable structure of the invention, the multi-layered structure comprises a stack of fuel cells comprising a plurality of fuel cells laid one upon another, said apparatus further comprising: cut-off means for cutting off a connection of the stack of fuel cells with a predetermined load for a preset time period; and concentration calculating means for calculating a concentration of the organic compound included in the reactant gas, based on the potential difference measured by the potential difference measurement means, in the preset time period when the predetermined load is disconnected from the stack of fuel cells by the cut-off means.

The concentration calculating means calculates the concentration of organic compound, for example, methanol, included in the reactant gas, based on the potential difference measured by the potential difference measurement means, in the preset time period when the predetermined load is disconnected from the stack of fuel cells by the cut-off means. This structure allows the organic compound included in the hydrogen-rich reactant gas to be detected using the stack of fuel cells for converting the chemical energy of the hydrogen-rich reactant gas to electrical energy. The cut-off means cuts off the connection of the stack of fuel cells with a predetermined load for a preset time period. The preset time required for measuring the potential difference between the electrodes under the no-load condition generally ranges from several to ten-odd milliseconds. When the predetermined load is a driving apparatus having relatively low response, such as a motor, the temporary, short-time interception does not affect the driving apparatus but allows continuous operation of the driving apparatus.

The invention is also directed to an apparatus for measuring a lower alcohol included in a hydrogen-containing reactant gas. The lower alcohol-detecting apparatus comprises: an electrolyte membrane; first and second electrodes with a catalyst carried thereon, the first and the second electrodes being arranged across the electrolyte membrane; a reactant gas supply conduit for supplying the reactant gas to the first electrode; an oxygen gas supply conduit for supplying an oxygen-containing gas to the second electrode; and potential difference measurement means for measuring a potential difference between the first and the second electrodes. The lower alcohol detected here may be methanol.

In the lower alcohol-detecting apparatus of this structure, a supply of reactant gas is fed to the first electrode via the reactant gas supply conduit, whereas a supply of oxygen-containing gas is fed to the second electrode via the oxygen gas supply conduit. The potential difference measurement means then measures a potential difference generated between the first and the second electrodes across the electrolyte membrane. Since the existence of lower alcohol in the reactant gas decreases the potential difference between the two electrodes, measurement of the potential difference gives the concentration of lower alcohol included in the reactant gas. The lower alcohol-detecting apparatus of the invention can accordingly determine the concentration of lower alcohol included in a hydrogen-rich gas containing only a trace amount of lower alcohol in an extremely large amount of hydrogen, like a gaseous fuel fed to the fuel cells.

The above objects are also realized by a method of detecting carbon monoxide included in a hydrogen-containing reactant gas. The method comprises the steps of:

(a) supplying the reactant gas to a first electrode, which is one of two electrodes having a catalyst carried thereon and being arranged across an electrolyte membrane;

(b) supplying an oxygen-containing gas to a second electrode, which is the other of the two electrodes; and (c) measuring a potential difference between the first and second electrodes while a predetermined load is connected to the first and second electrodes.

The invention is also directed to a method of detecting an organic compound included in a hydrogen-containing reactant gas. The method comprises the steps of:

(g) supplying the reactant gas to a first electrode, which is one of two electrodes having a catalyst carried thereon and being arranged across an electrolyte membrane;

(h) supplying an oxygen-containing gas to a second electrode, which is the other of the two electrodes; and (i) measuring a potential difference between the first and second electrodes.

In accordance with another aspect of the invention, the method of measuring an organic compound included in a hydrogen-containing reactant gas comprises the steps of:

(n) supplying the reactant gas to a first electrode in each layer unit of a multi-layered structure, the multi-layered structure comprising a plurality of layer units laid one upon another, each the layer unit comprising an electrolyte membrane and first and second electrodes having a catalyst carried thereon and arranged across the electrolyte membrane;

(o) supplying an oxygen-containing gas to the second electrode in the each layer unit of the multi-layered structure; and (p) measuring a potential difference between the first electrode proximate to a first end of the multi-layered structure and the second electrode proximate to a second end of the multi-layered structure, which is opposite to the first end.

In this method, the multi-layered structure is typically a stack of fuel cells comprising a plurality of fuel cells laid one upon another. The method preferably comprises the further steps of:

(q) cutting off a connection of the stack of fuel cells with a predetermined load for a preset time period; and (r) calculating a concentration of the organic compound included in the reactant gas, based on the potential difference measured in the step (p), in the preset time period when the predetermined load is disconnected from the stack of fuel cells in the step (q).

The invention is further directed to a method of detecting a lower alcohol included in a hydrogen-containing reactant gas. The method comprises the steps of:

(s) supplying the reactant gas to a first electrode, which is one of two electrodes having a catalyst carried thereon and being arranged across an electrolyte membrane;

(t) supplying an oxygen-containing gas to a second electrode, which is the other of the two electrodes; and (u) measuring a potential difference between the first and second electrodes.

These and other objects, features, aspects, and advantages of the present invention will become more apparent from the following detailed description of the preferred embodiments with the accompanying drawings.

DESCRIPTION OF THE PREFERRED EMBODIMENT

First through fifth embodiments according to the invention described below are related to the apparatus for measuring carbon monoxide.

Figure 1:
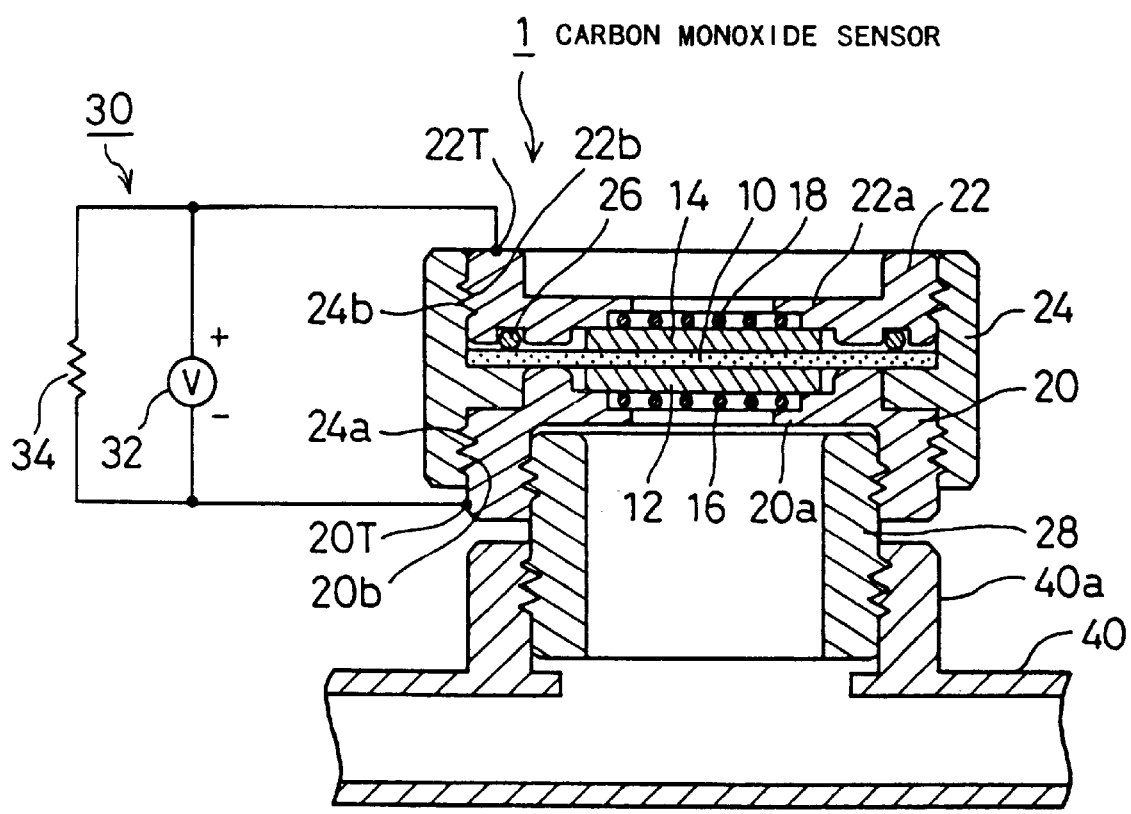
FIG. 1 is a vertical cross sectional view schematically illustrating a carbon monoxide sensor 1 as a first embodiment according to the invention.

FIG. 1 is a vertical cross sectional view illustrating a carbon monoxide sensor 1 as a first embodiment according to the invention. The carbon monoxide sensor 1 includes an electrolyte membrane 10, a pair of electrodes 12 and 14 arranged across the electrolyte membrane 10 to form a sandwich structure, a pair of meshed metal plates 16 and 18 disposed across the sandwich structure to prevent deflection of the sandwich structure, a pair of holders 20 and 22 for supporting the sandwich structure as well as the pair of meshed metal plates 16 and 18, and an insulating member 24 for connecting the holders 20 and 22 with each other under electrically insulating conditions.

The electrolyte membrane 10 is composed of solid polymer material, such as fluororesin, to be proton-conductive.

The electrodes 12 and 14 are made of carbon cloth woven of carbon fibers, where carbon powder with platinum catalyst carried thereon is inserted into pores of the carbon cloth.

The electrolyte membrane 10 and the pair of electrodes 12 and 14 are joined together according to one of the following methods:

(1) Catalyst powder prepared in advance by making platinum carried on the surface of carbon powder is applied onto the surface of electrode bases (carbon cloth or carbon paper). The electrolyte membrane 10 and the electrode bases are then integrated by hot pressing.

(2) Catalyst powder prepared in advance by making platinum carried on the surface of carbon powder is applied onto the surface of electrode bases. The electrolyte membrane 10 and the electrode bases are subsequently joined together by means of a solution of proton-conductive solid polymer.

(3) Catalyst powder prepared in advance by making platinum carried on the surface of carbon powder is dispersed in an appropriate organic solvent to form paste. The paste is applied on the surface of the electrolyte membrane 10 by a known technique, like screen printing. The electrolyte membrane 10 and electrode bases are subsequently integrated by hot pressing.

(4) Platinum is carried on the surface of the electrolyte membrane 10 by sputtering, vapor deposition, CVD, PVD, or another method of thin film formation. The electrolyte membrane 10 and electrode bases are subsequently integrated by hot pressing.

Carbon powder with platinum catalyst carried thereon is prepared in the following manner. An aqueous solution of chloroplatinic acid is mixed with sodium thiosulfate to yield an aqueous solution of platinum sulfite complex. Hydrogen peroxide is added dropwise to the aqueous solution of platinum sulfite with stirring, so that platinum colloidal particles are deposited in the aqueous solution. Carbon black working as a carrier is then added to the aqueous solution with stirring, so that the platinum colloidal particles adhere to the surface of carbon black. Examples of applicable carbon black include Vulcan XC-72 (trade name by CABOT Corp., the USA) and Denka Black (trade name by DENKI KAGAKU KOGYO K.K). The carbon black with platinum particles adhering thereto is separated by filtration under reduced pressure or pressure filtration of the aqueous solution, washed repeatedly with deionized water, and completely dried at room temperature. The dried carbon black aggregate is ground with a grinder and heated in a reducing hydrogen atmosphere at 250° C. through 350° C. for approximately 2 hours for reduction of platinum on the carbon black and complete removal of the remaining chlorine.

The carrying density of platinum onto carbon black in the resulting platinum catalyst powder thus prepared, that is, the ratio of the weight of platinum carried on the carbon surface to the weight of carbon, is adjusted by varying the ratio of the quantity of chloroplatinic acid to the quantity of carbon black. Preparation of platinum catalyst powder is not limited to this method, but any other method is applicable as long as it ensures sufficient catalytic activities.

For the clarity of explanation, catalyst powder prepared above contains only platinum as a catalytic component. An alloy catalyst containing platinum as a primary component and one or the plural selected out of the group including ruthenium, nickel, cobalt, vanadium, palladium, indium, iron, chromium, and manganese, as a secondary component may, however, be used in place of platinum catalyst.

Preparation of platinum-ruthenium catalyst powder, that is, carbon black with platinum-ruthenium alloy catalyst carried thereon, is explained as an example of alloy catalyst. The platinum catalyst powder (carbon black with platinum catalyst carried thereon) prepared in the above manner is dispersed in deionized water with stirring. An aqueous solution of ruthenium chloride in limited amounts is added to the dispersion with stirring, and an aqueous solution of sodium carbonate in limited amounts is further added to the dispersion with stirring, so that ruthenium particles are deposited on the platinum catalyst-carrying carbon black. The platinum catalyst-carrying carbon black with ruthenium particles adhering thereto is separated by filtration under reduced pressure or pressure filtration of the solution mixture, washed repeatedly with deionized water, and sufficiently dried at room temperature. The dried carbon black aggregate is ground with a grinder and heated in a reducing hydrogen atmosphere at 250° C. through 350° C. for approximately 2 hours for reduction of platinum and ruthenium on the carbon black and complete removal of the remaining chlorine taken up during the deposition of ruthenium. The carbon black with platinum and ruthenium carried thereon is heated in a stream of inert gas (nitrogen or argon) at 800° C. through 900° C. for approximately 1 hour. This heating process makes an alloy of platinum and ruthenium on the carbon black and completes the platinum-ruthenium catalyst powder, that is, carbon black with platinum-ruthenium alloy catalyst carried thereon.

The amounts of platinum and ruthenium carried on carbon black are adjusted by varying the quantity of platinum-carrying carbon black and the quantity of ruthenium chloride. Preparation of platinum-ruthenium catalyst powder is not limited to this method, but any other method is applicable as long as it ensures sufficient catalytic activities.

The preferable area of electrodes 12 and 14 ranges from 0.1 through 1.0 $cm^2$.

The meshed metal plates 16 and 18 have structure of allowing a gas to be flown into the electrodes 12 and 14. Preferable material for the meshed metal plates 16 and 18 has excellent electrical conductivity and good rust preventing properties and does not cause hydrogen brittleness; for example, titanium and stainless steel. Alternatively, the metal plates 16 and 18 may be meshed copper plates having surface coated with (for example, plated with) a metal like gold, platinum, or titanium. As long as the required properties including excellent electrical conductivity are satisfied, porous carbon plates, foamed nickel plates, and engineering plastics having surface coated with (for example, plated with) a metal like gold, platinum, or titanium may also be applicable as the metal plates 16 and 18.

The holders 20 and 22 respectively have flanges 20a and 22a projected inward from the cylindrical holder structures 20 and 22. The electrolyte membrane 10 and the pair of electrodes 12 and 14 as well as the meshed metal plates 16 and 18 are supported by these flanges 20a and 22a of the holders 20 and 22. Preferable material for the holders 20 and 22 has excellent electrical conductivity and good rust preventing properties and does not cause hydrogen brittleness; for example, titanium and stainless steel. As long as the required properties including excellent electrical conductivity are satisfied, copper plates and dense carbon plates or engineering plastics having surface coated with (for example, plated with) a metal like gold, platinum, or titanium may also be applicable as the holders 20 and 22.

The holder 22 is provided with an O-ring 26, which comes into contact with the electrolyte membrane 10 and prevents an atmosphere of one electrode from leaking to the other electrode. Another structure of ensuring the sealing properties may also be applicable instead of the O-ring 26; for example, an end portion of the electrolyte membrane 10 is applied to the holder 22 directly via an adhesive or by means of thermal contact bonding.

The holders 20 and 22 respectively have, on the circumference thereof, outer screw threads 20b and 22b, which mate and engage with internal screw threads 24a and 24b formed inside the insulating member 24. Engagement of the mating screw threads 20b,22b and 24a,24b connects the holders 20 and 22 with each other, where the holders 20 and 22 securely support the sandwich structure of electrode 12-electrolyte membrane 10-electrode 14 placed therebetween. Preferable material for the insulating member 24 is, for example, Teflon.

The carbon monoxide sensor 1 further includes a gas flow conduit 28 joined with one holder 20 through engagement of mating screw threads. The gas flow conduit 28 leads a gaseous fuel or object gas to be detected into the electrode 12 and is composed of insulating material. The other holder 22 does not connect with any specific gas conduit, but the electrode 14 is exposed to the atmosphere.

The carbon monoxide sensor 1 is also provided with a circuit 30, which electrically connects detection terminals 20T and 22T of the holders 20 and 22 with each other. The circuit 30 includes a voltmeter 32 and a resistor 34 for adjusting load current, which are arranged in parallel between the detection terminals 20T and 22T. Connection of the voltmeter 32 is determined to give negative polarity to the detection terminal 20T of the holder 20 on the side of the electrode 12 exposed to a gaseous fuel and positive polarity to the detection terminal 22T of the holder 22 on the side of the electrode 14 exposed to the atmosphere. Signals of the voltmeter 32 are output to an external control system.

The carbon monoxide sensor 1 thus constructed is linked through engagement of mating screw threads with a branched opening 40a of a gaseous fuel conduit 40 included in a fuel cell generator (not shown). The carbon monoxide sensor 1 is used for determining the concentration of carbon monoxide included in a supply of gaseous fuel fed to fuel cells (not shown).

The following description regards the process of detecting carbon monoxide included in a hydrogen-rich gaseous fuel (object gas to be detected) with the carbon monoxide sensor 1. A supply of gaseous hydrogen included in the hydrogen-rich gaseous fuel is fed to the electrode 12 of the carbon monoxide sensor 1, while a supply of oxygen included in the atmosphere is fed to the electrode 14. Reactions expressed by Equations (6) and (7) below accordingly proceed on the surface of the electrodes 12 and 14 across the electrolyte membrane 10:

$$H_2 \rightarrow 2H^+ + 2e^- \quad (6)$$

$$2H^+ + 2e^- + (\tfrac{1}{2})O_2 \rightarrow H_2O \quad (7)$$

These reactions are identical with those in fuel cells, which uses hydrogen and oxygen as fuels to generate electrical energy. An electromotive force is thus generated between the electrodes 12 and 14. Since the resistor 34 is connected to the electrodes 12 and 14 in this embodiment, the voltmeter 32 measures the potential difference between the electrodes 12 and 14 generated when a predetermined load is placed between the electrodes 12 and 14 and certain electric current is flown through the circuit. The potential difference decreases with an increase in concentration of carbon monoxide included in the gaseous fuel. This phenomenon is ascribed to the following reasons.

The reaction expressed by Equation (6) given above proceeds on the electrode 12, in which carbon powder with platinum catalyst carried thereon is inserted. Carbon monoxide existing in the gaseous fuel is adsorbed by the catalyst and interferes with the catalytic action, that is, poisons the catalyst. The degree of poisoning is large for the high concentration of carbon monoxide included in the gaseous fuel and small for the low concentration of carbon monoxide. The potential difference between the detection terminals 20T and 22T is measured, while the reactions expressed by Equations (6) and (7) continuously proceed on the electrodes 12 and 14. Since the potential difference reflects the concentration of carbon monoxide included in the gaseous fuel, the measurement of potential difference determines the concentration of carbon monoxide included in the gaseous fuel. The resistor 34 connecting one detection terminal 20T with the other detection terminal 22T allows the reactions of Equations (6) and (7) to continuously proceed on the electrodes 12 and 14, while the potential difference is measured between the detection terminals 20T and 22T.

Figure 2:
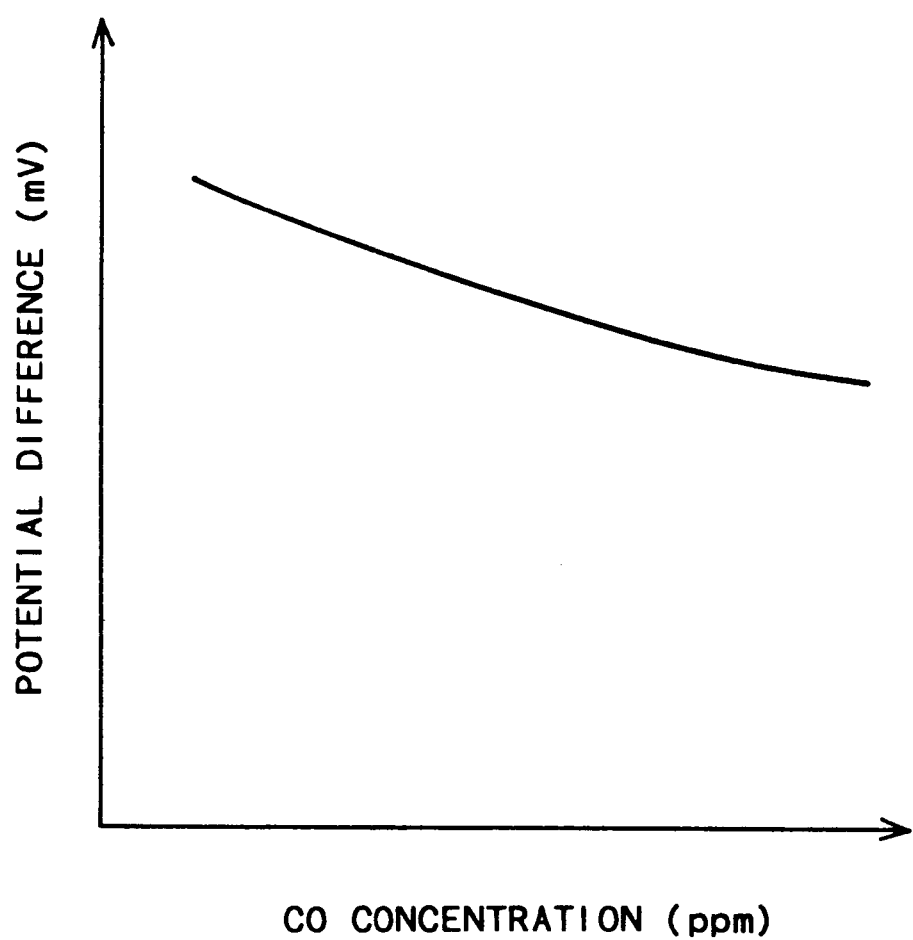
FIG. 2 is a graph showing a relationship between the concentration of carbon monoxide included in the gaseous fuel and the potential difference measured by the voltmeter 32.

A relationship between the concentration of carbon monoxide and the measurement of the voltmeter 32 is determined previously using gas containing known concentrations of carbon monoxide. The concentration of carbon monoxide included in the gaseous fuel is then determined according to this relationship. In accordance with a concrete structure, a map representing a relationship between the concentration of carbon monoxide included in the gaseous fuel and the potential difference measured by the voltmeter 32, for example, a map as shown in FIG. 2, is stored previously in a ROM of an electronic control unit. The electronic control unit refers to the map and executes logic operations to determine the concentration of carbon monoxide. The sensitivity of detection is not affected by the existence of hydrogen in this process of determining the concentration of carbon monoxide. The concentration of carbon monoxide included even in the hydrogen-rich reactant gas, such as a supply of gaseous fuel fed to fuel cells, can thus be determined with high precision.

In the carbon monoxide sensor 1, while one electrode 12 receives a supply of gaseous fuel, the other electrode 14 is exposed to the atmosphere. This does not require any specific gas supply conduit on the electrode 14, thereby reducing the size of the whole carbon monoxide sensor 1.

In the first embodiment, the electronic control unit reads the voltage measured with the voltmeter 32 of the carbon monoxide sensor 1 and determines the concentration of carbon monoxide included in the gaseous fuel by referring to the map as shown in FIG. 2. Another possible structure outputs a predetermined signal showing that the gaseous fuel contains carbon monoxide of not less than a predetermined concentration when the voltage measured with the voltmeter 32 is not greater than a predetermined value. According to a concrete application, the electronic control unit compares with the voltage measured with the voltmeter 32 with a predetermined value, which is stored previously in a ROM of the electronic control unit, and outputs an L-level signal for the voltage of greater than the predetermined value and an H-level signal for the voltage of not greater than the predetermined value.

The carbon monoxide sensor 1 has temperature dependence; that is, the output voltage for a fixed concentration of carbon monoxide is varied depending upon the temperature of the carbon monoxide sensor 1. The temperature of the carbon monoxide sensor 1 may be different from the temperature of fuel cells by their relative positions. A preferable structure thus previously determines temperature-output voltage and carbon monoxide concentration-output voltage characteristics, and corrects the output voltage based on the temperature of the carbon monoxide sensor 1 for determining the concentration of carbon monoxide with further enhanced precision.

Figure 3:
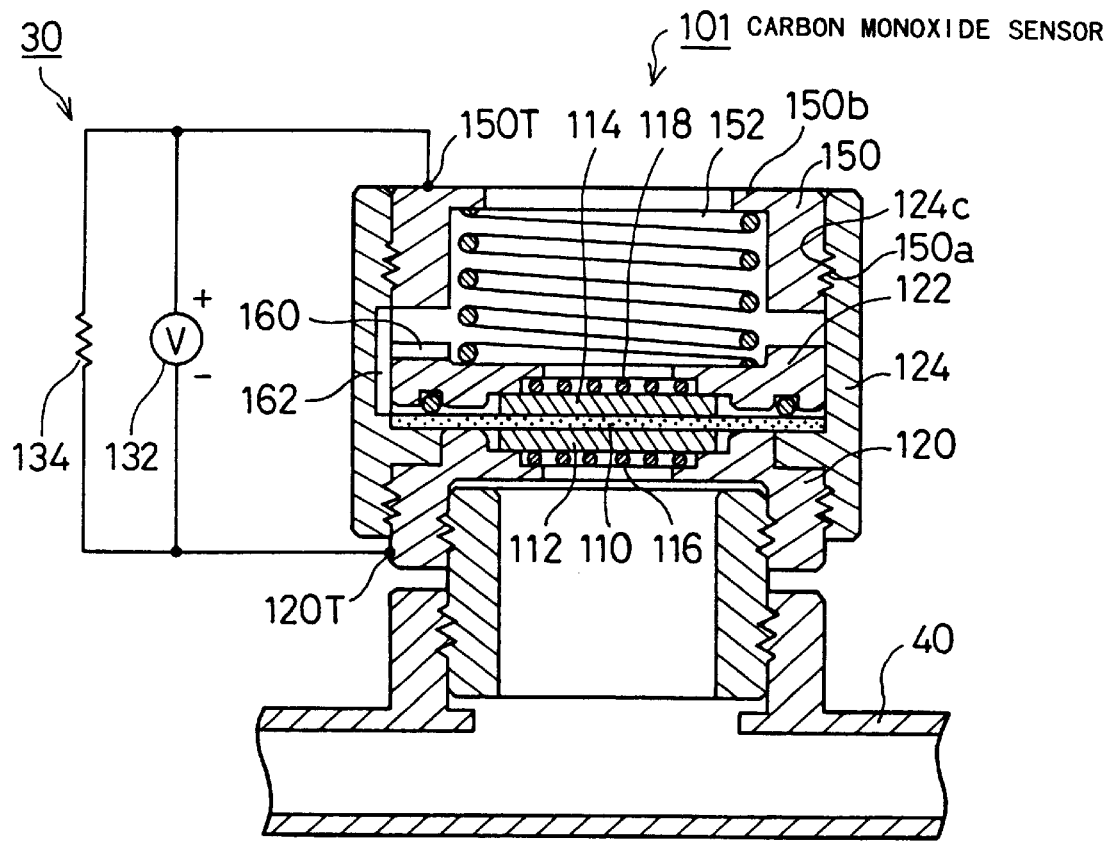
FIG. 3 is a vertical cross sectional view schematically illustrating another carbon monoxide sensor 101 as a second embodiment according to the invention.

FIG. 3 is a vertical cross sectional view illustrating another carbon monoxide sensor 101 as a second embodiment according to the invention. Like the carbon monoxide sensor 1 of the first embodiment, the carbon monoxide sensor 101 of the second embodiment includes an electrolyte membrane 110, a pair of electrodes 112 and 114 arranged across the electrolyte membrane 110 to form a sandwich structure, a pair of meshed metal plates 116 and 118 disposed across the sandwich structure, lower and upper holders 120 and 122 for supporting the sandwich structure as well as the pair of meshed metal plates 116 and 118, an insulating member 124 for connecting the lower holder 120 with the upper holder 122 under electrically insulating conditions, and a third holder 150 disposed above the upper holder 122.

Unlike the holder 22 of the first embodiment, the upper holder 122 exposed to the atmosphere does not have a screw thread on the circumference thereof, but is fitted in the insulating member 124. The insulating member 124 is formed higher than the insulating member 24 of the first embodiment.

The third holder 150 has, on the circumference thereof, a screw thread 150a, which engages with a mating screw thread 124c formed inside the insulating member 124. Engagement of the mating screw threads 150a and 124c allows the third holder 150 to be securely held inside the insulating member 124. A flange 150b is projected inward from the top end of the third holder 150, and a spring 152 is arranged to have one end in contact with the bottom face of the flange 150b. The other end of the spring 152 comes into contact with the upper holder 122, and presses down the sandwich structure of electrode 114-electrolyte membrane 110-electrode 112 indirectly via the upper holder 122.

The third holder 150 is made of the same material as the lower and upper holders 120 and 122, whereas the spring 152 is made of steel stock having excellent electrical conductivity. The third holder 150 is thus electrically connected to the upper holder 122 via the spring 152. The third holder 150 is further provided with a detection terminal 150T, which is connected with a detection terminal 120T of the lower holder 120 by a circuit 130. The circuit 130 includes a voltmeter 132 and a resistor 134 for adjusting load current, like the circuit 30 of the first embodiment.

Figure 4:
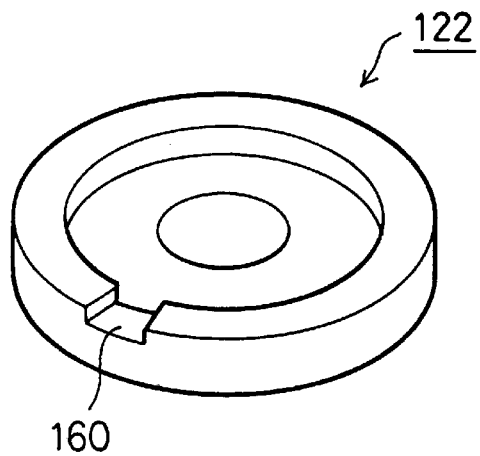
FIG. 4 is a perspective view illustrating an upper holder 122 disposed in the carbon monoxide sensor 101.

The upper holder 122 has a notched groove 160 on the upper circumference thereof as clearly seen in FIG. 4, while the insulating member 124 has a vertical groove 162 formed on the inside wall thereof as shown in FIG. 3. The vertical groove 162 runs from a lower end of the third holder 150 to a lower end of the upper holder 122, which is located at the lower-most position. The vertical groove 162 connects with the notched groove 160 formed on the upper holder 122. The notched groove 160 and the vertical groove 162 function as a safety valve for relieving the pressure of gaseous fuel abnormally heightened. Operation of safety valve function is described more in detail.

FIG. 3 shows the state in which the upper holder 122 is pressed down to its lower-most position by the pressing force of the spring 152. In this state of FIG. 3 (hereinafter referred to as the normal state), an gaseous fuel supplied through the electrode 112 gradually leaks through a space between the lower holder 120 and the electrode 112 into a space between the lower holder 120 and the electrolyte membrane 110 and passes through a space between the side face of the electrolyte membrane 110 and the inner wall of the insulating member 124, whereas an O-ring 126 effectively prevents the gaseous fuel from leaking into the electrode 114.

Figure 5:
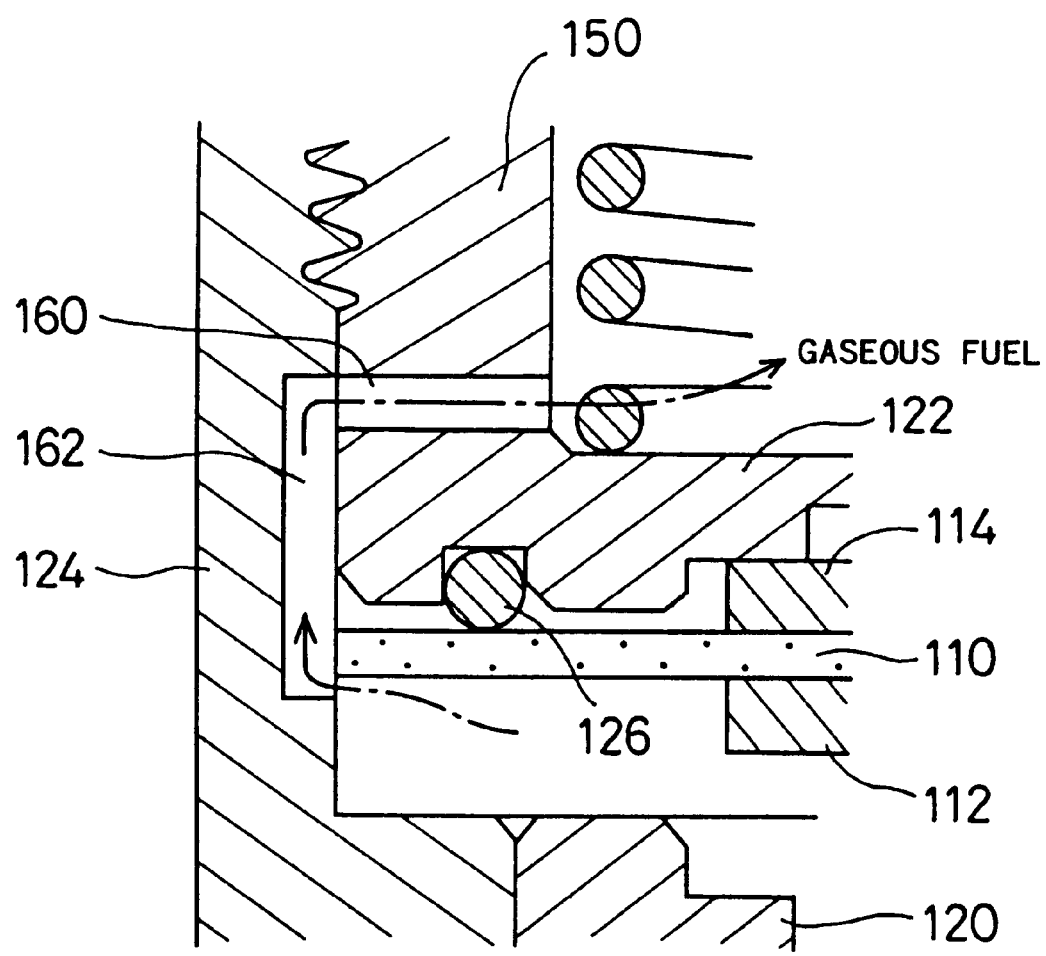
FIG. 5 is an enlarged cross sectional view illustrating a gas flow in the carbon monoxide sensor 101 under a condition of abnormally heightened pressure.

When the pressure of gaseous fuel abnormally increases from the normal state, the sandwich structure of electrode 112-electrolyte membrane 110-electrode 114 and the upper holder 122 receive the abnormally heightened pressure and press the spring 152 upward. When the upward force exceeds the pressing force of the spring 152, the sandwich structure and the upper holder 122 move upward in the vertical direction until the upper end of the upper holder 122 comes into contact with the lower end of the third holder 150, as shown in the enlarged cross sectional view of FIG. 5. A flow of the gaseous fuel in this state is shown by the one-dot chain line in FIG. 5. Since the side face of the electrolyte membrane 110 is located above the lower end of the vertical groove 162 as shown in FIG. 5, the gaseous fuel flows along the side face of the electrolyte membrane 110 into the vertical groove 162 and passes through the notched groove 160 formed on the upper holder 122 towards the electrode 114 exposed to the atmosphere. The gaseous fuel having abnormally heightened pressure is eventually released to the atmosphere.

When the pressure of gaseous fuel is decreased to the normal level by the release of gaseous fuel, the pressing force of the spring 152 again overcomes the upward force of the gaseous fuel. In this state, the gaseous fuel is not released to the atmosphere, but is sealed on the side of the electrode 112.

Like the carbon monoxide sensor 1 of the first embodiment, the carbon monoxide sensor 101 of the second embodiment thus constructed can determine the concentration of carbon monoxide by measuring an electromotive force generated between the electrodes 112 and 114 with the voltmeter 132 of the circuit 130. The sensitivity of detection is not affected by the existence of hydrogen, and the concentration of carbon monoxide included in the gaseous fuel can thus be determined with high precision like the first embodiment.

When the pressure of gaseous fuel or object gas abnormally increases, the carbon monoxide sensor 101 of the second embodiment releases the heightened pressure to the atmosphere via the vertical groove 162 and the notched groove 160, thereby effectively canceling the abnormal increase of gas pressure which may cause some troubles or problems.

In the carbon monoxide sensor 101 of the second embodiment, the electrode 112 is electrically disconnected from the lower holder 120 under the condition of abnormally heightened pressure as shown in FIG. 5. The voltage=0 [V] measured by the voltmeter 132 accordingly implies an operation of safety valve function to release the abnormally heightened gas pressure to the atmosphere.

The structure of detecting an operation of safety valve function by an electric signal gives the secondary effects as below. Operation of commercially available safety valves used as general gas-piping parts can not be detected electrically, but is checked by existing or non-existing sound of gas discharged from a gas cock. Only when a user is near the gas cock, he notices an operation of the safety valve and takes a required measure. The carbon monoxide sensor 101 of the second embodiment, however, can electrically detect an operation of safety valve function. For example, a fuel cell generator system with such a carbon monoxide sensor receives an electric signal representing an operation of safety valve function and stops or limits a supply of fuels (methanol and water) to a methanol reformer, thereby automatically checking an increase in pressure of gaseous fuel.

According to another possible structure, an impedance between the detection terminal 120T of the lower holder 120 and the detection terminal 150T of the third holder 150 is measured. In this modified structure, infinite impedance implies an operation of safety valve function, and a signal representing an operation of safety valve function is output to the control system.

Figure 6:
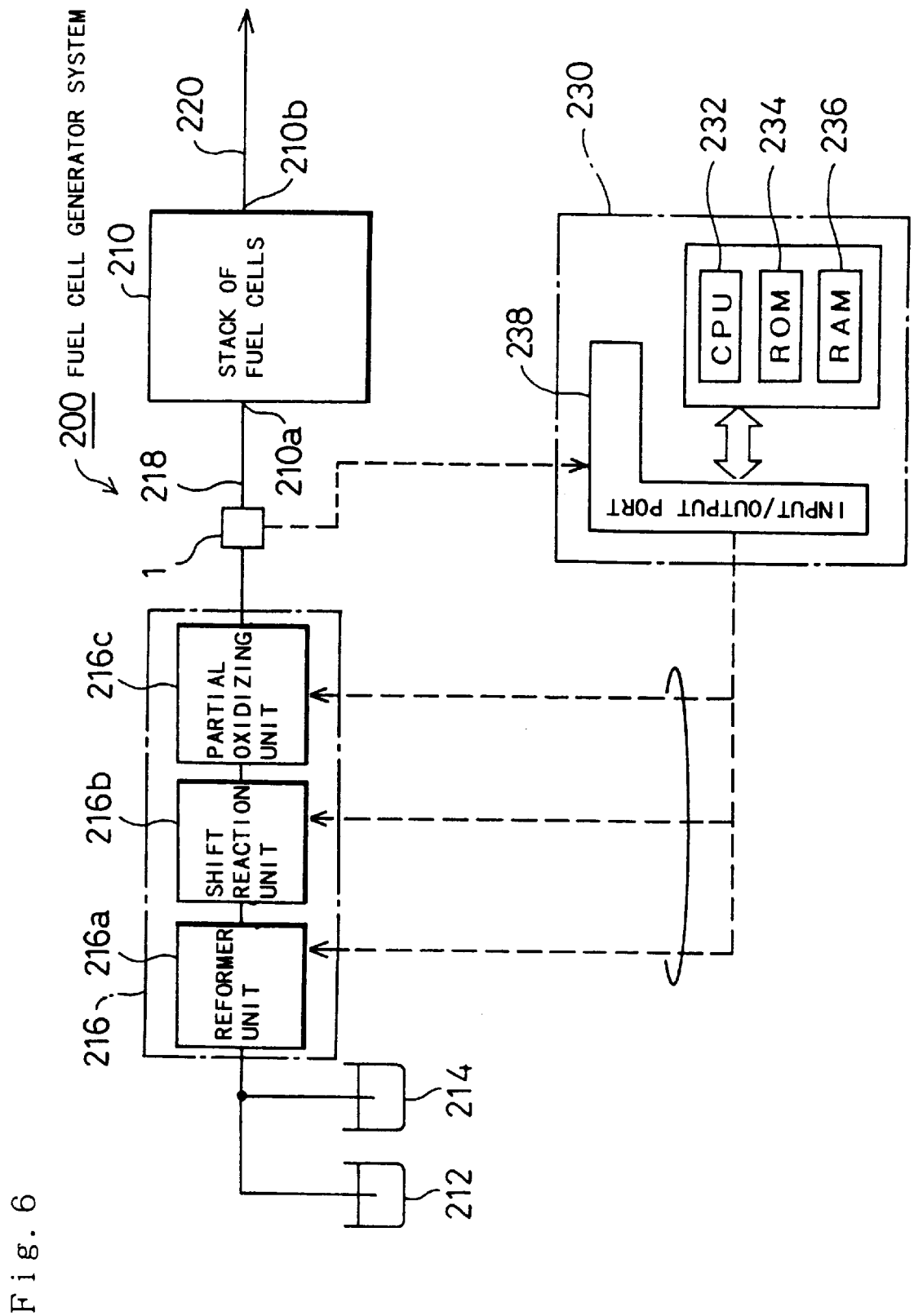
FIG. 6 is a block diagram schematically illustrating structure of a fuel cell generator system 200 with the carbon monoxide sensor 1 of the first embodiment, as a third embodiment according to the invention.

The carbon monoxide sensor described above can be incorporated in a fuel cell generator system. FIG. 6 is a block diagram illustrating structure of a fuel cell generator system 200 with the carbon monoxide sensor 1 of the first embodiment, as a third embodiment according to the present invention.

The fuel cell generator system 200 includes a stack of polymer electrolyte fuel cells 210 for generating electrical energy, a reformer 216 for generating hydrogen-rich gas from methanol stored in a methanol reservoir 212 and water stored in a water reservoir 214, a gaseous fuel supply conduit 218 for feeding the hydrogen-rich gas generated by the reformer 216 as a gaseous fuel to the stack of fuel cells 210, and a gaseous fuel discharge conduit 220 for discharging the residual gas from the stack of fuel cells 210. The fuel cell generator system 200 is further provided with the carbon monoxide sensor 1 described above in the middle of the gaseous fuel supply conduit 218. An electronic control unit 230 receives output signals of the carbon monoxide sensor 1 and executes a variety of control processes.

Figure 7:
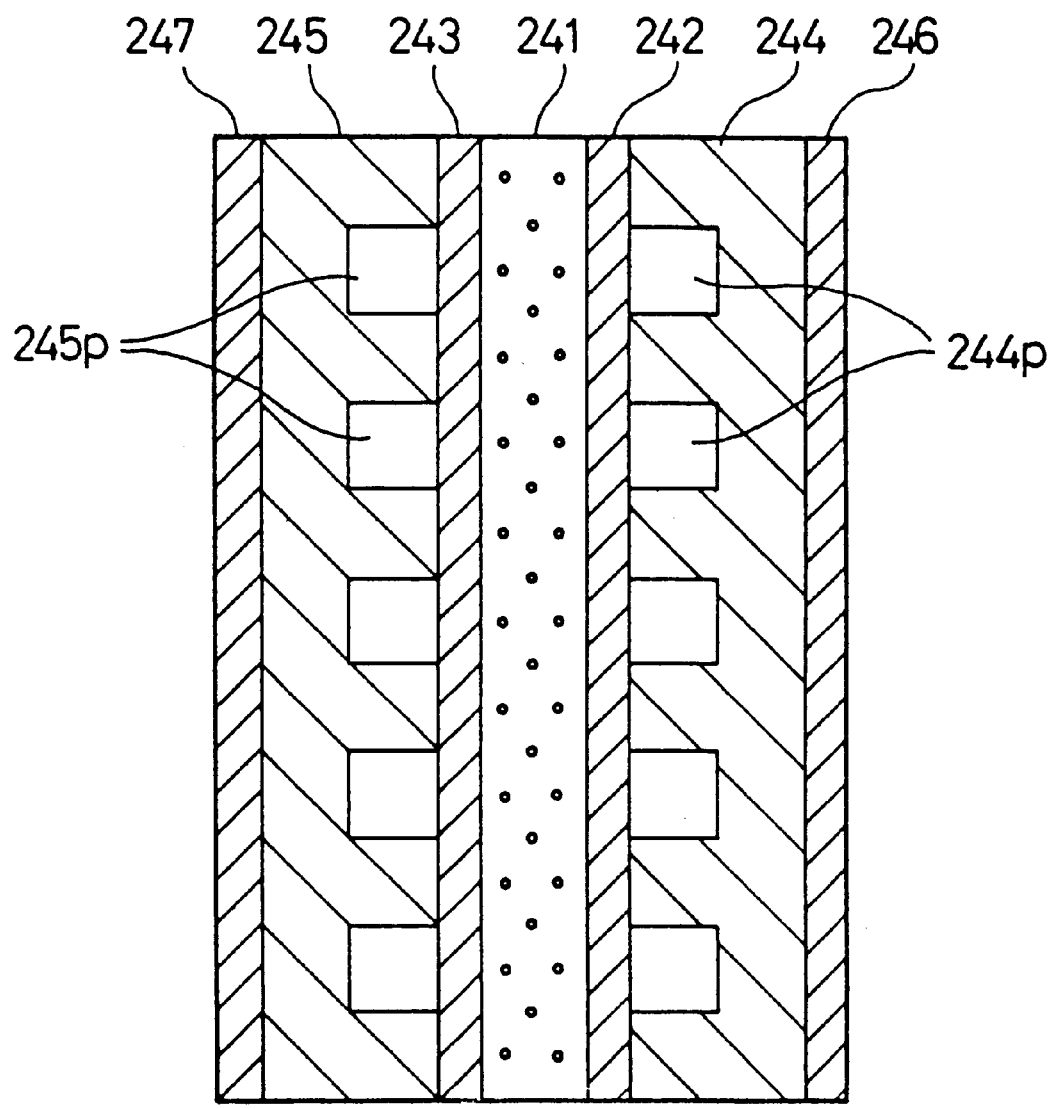
FIG. 7 is a cross sectional view illustrating a unit cell structure in a stack of fuel cells 210.

The stack of fuel cells 210 includes a plurality of polymer electrolyte fuel cells, whose unit cell structure is shown in FIG. 7. Each unit fuel cell includes an electrolyte membrane 241, an anode 242 and a cathode 243 arranged across the electrolyte membrane 241 to form a sandwich structure and work as gas diffusion electrodes, first and second separators 244 and 245 disposed across the sandwich structure and combined with the anode 242 and the cathode 243 to constitute flow paths of gaseous fuel and oxygen-containing gas, and first and second current collectors 246 and 247 disposed respectively outside the first and the second separators 244 and 245 to work as current-collecting electrodes of the anode 242 and the cathode 243.

The electrolyte membrane 241 is composed of solid polymer material, such as fluororesin, to be proton-conductive and shows a favorable electrical conductivity under the wet conditions. The anode 242 and the cathode 243 are made of carbon cloth woven of carbon fibers, where carbon powder with platinum catalyst or platinum-containing alloy catalyst carried thereon is inserted into the surface of the carbon cloth close to the electrolyte membrane 241 and into pores of the carbon cloth. The electrolyte membrane 241, the anode 242, and the cathode 243 are joined together to form a sandwich structure of anode 242-electrolyte membrane 241-cathode 243, in the same manner as the electrolyte membrane 10 and the two electrodes 12 and 14 in the carbon monoxide sensor 1 of the first embodiment.

The first separator 244 has a plurality of ribs, which constitute, in connection with the surface of the anode 242, a plurality of first channels 244p allowing flows of gaseous fuel. The second separator 245 also has a plurality of ribs, which constitute, in connection with the surface of the cathode 243, a plurality of second channels 245p allowing flows of oxygen-containing gas.

Each unit fuel cell in the stack of fuel cells 210 has the structure described above. In the actual configuration of the stack of fuel cells 210, plural sets of first separator 244/ anode 242/ electrolyte membrane 241/ cathode 243/ second separator 245 are laid one upon another, and the first and the second current collectors 246 and 247 are disposed outside the plural sets.

The gaseous fuel supply conduit 218 connects the reformer 216 with an anode-side gas inlet 210a of the stack of fuel cells 210. According to a concrete structure, the anode-side gas inlet 210a is connected to a manifold (not shown) and further to the plurality of first channels 244p for the flows of gaseous fuel in the stack of fuel cells 210 via the manifold. An anode-side gas outlet 210b of the stack of fuel cells 210 is also connected to another manifold (not shown) and further to the plurality of first channels 244p in the stack of fuel cells 210 via the manifold. The direction of connection of the gas outlet 210b is opposite to the direction of connection of the gaseous fuel supply conduit 218.

The reformer 216 includes: a reformer unit 216a allowing the reaction (expressed by Equation (1) above) of decomposing methanol to carbon monoxide and hydrogen and the reaction (expressed by Equation (2) above) of generating carbon dioxide and hydrogen from water and carbon monoxide generated by the decomposition reaction; a shift reaction unit 216b for making the residual, non-reacted carbon monoxide in the reformer unit 216a further react with water; and a partial oxidizing unit (also called as selective oxidizing unit) 216c for oxidizing the residual, non-reacted carbon monoxide in the shift reaction unit 216b. The units 216a through 216c of the reformer 216 are respectively connected to the electronic control unit 230.

The electronic control unit 230 is constructed as a logic circuit with a microcomputer. According to a concrete structure, the electronic control unit 230 includes: a CPU 232 for executing a variety of operations according to preset control programs; a ROM 234, in which control programs and control data required for the execution of various operations by the CPU 232 are previously stored; a RAM 236, which various data required for the execution of various operations by the CPU 232 are temporarily written in and read from; and an input/output port 238 for receiving output signals from the carbon monoxide sensor 1 and outputting control signals to the reformer unit 216a, the shift reaction unit 216b, and the partial oxidizing unit 216c of the reformer 216.

In the drawing of FIG. 6, only the gas system on the anode's side is shown and that on the cathode's side is omitted.

The CPU 232 of the electronic control unit 230 thus constructed receives output signals from the carbon monoxide sensor 1 and controls the reformer unit 216a, the shift reaction unit 216b, and the partial oxidizing unit 216c of the reformer 216 according to the output signals, so as to reform the quality of hydrogen-rich gas used as gaseous fuel.

Figure 8:
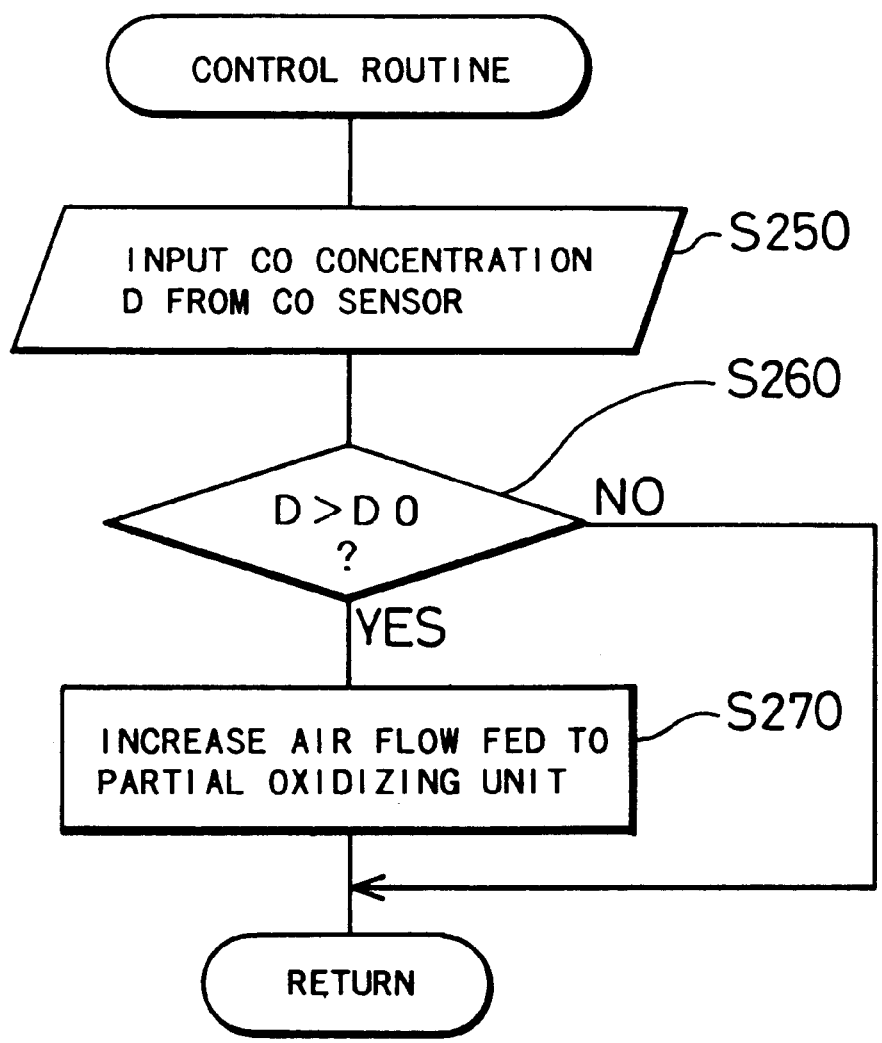
FIG. 8 is a flowchart showing a control routine executed by the CPU 232 of the electronic control unit 230 in the third embodiment.

FIG. 8 is a flowchart showing a control routine of reforming the hydrogen-rich gas. The control routine is repeatedly executed at predetermined time intervals. When the program enters the routine, the CPU 232 stores an output voltage from the voltmeter 32 of the carbon monoxide sensor 1 as a measured concentration D of carbon monoxide into the RAM 236 at step S250. The measured concentration D of carbon monoxide is then compared with a predetermined level D0 at step S260. In this embodiment, the predetermined level D0 is set equal to 20 [ppm] under an operating condition that the gas consumption ratio on the anode's side is 80[%].

When the measured concentration D of carbon monoxide is greater than the predetermined level D0 at step S260, the CPU 232 determines that the concentration of carbon monoxide from the reformer 216 is too high and executes a required process to lower the concentration of carbon monoxide discharged from the reformer 216.

Affirmative answer at step S260 leads the program to step S270, at which the CPU 232 transmits a control signal to the partial oxidizing unit 216c of the reformer 216 to increase a flow of air fed into the partial oxidizing unit 216c. The partial oxidizing unit 216c is driven at temperatures of 100° C. through 200° C. An increase in air flow fed into the reformed gas accelerates the reaction of oxidizing carbon monoxide included in the reformed gas to carbon dioxide. This results in lowering the concentration of carbon monoxide included in the reformed gas discharged from the partial oxidizing unit 216c. The program then goes to RETURN and exits from the control routine.

When the measured concentration D of carbon monoxide is not greater than the predetermined level D0 at step S260, on the other hand, the CPU 232 determines that the concentration of carbon monoxide from the reformer 216 is at an appropriate level. The program then goes to RETURN and exits from this control routine.

In the fuel cell generator system 200 of the third embodiment, the carbon monoxide sensor 1 determines the concentration of carbon monoxide included in the hydrogen-rich gas supplied to the stack of fuel cells 210. When the measured concentration D of carbon monoxide is greater than the predetermined level D0, the CPU 232 increases the flow of air fed into the partial oxidizing unit 216c of the reformer 216. This effectively lowers the concentration of carbon monoxide included in the hydrogen-rich gas fed to the stack of fuel cells 210, thereby relieving the catalyst poisoning in the stack of fuel cells 210.

An increase in the air flow fed into the reformed gas in the partial oxidizing unit 216c accelerates the oxidation reaction shown below:

$$2CO + O_2 \rightarrow 2CO_2$$

$$2H_2 + O_2 \rightarrow 2H_2O$$

Such oxidation reaction relatively lowers the partial pressure of hydrogen included in the reformed gas. A relative decrease in partial pressure slightly lowers the output voltage from the stack of fuel cells 210. In a preferable structure, when the measured concentration D of carbon monoxide is restored to be smaller than the predetermined level D0, the air flow into the partial oxidizing unit 216c is returned to a stationary level.

In the structure of the third embodiment, the concentration of carbon monoxide included in the reformed gas is lowered by controlling the air flow fed into the partial oxidizing unit 216c. Other methods may, however, be applied to lower the concentration of carbon monoxide included in the reformed gas; for example, increasing the reaction temperature in the partial oxidizing unit 216c, increasing the reaction temperature in the reformer unit 216a, or controlling the reaction temperature in the shift reaction unit 216b.

The predetermined level D0 used for the comparison at step S260 depends upon the specifications of polymer electrolyte fuel cells (temperature of operation, type of catalyst, and gas consumption ratio). The predetermined level D0 is set by examining effects of a gaseous fuel containing a known concentration of carbon monoxide and flown into the fuel cell generator system (for example, a tank gas containing a known concentration of carbon monoxide), on the stack of fuel cells 210.

The carbon monoxide sensors 1 and 101 described in the first and the second embodiments have a predetermined sensitivity of detecting carbon monoxide. The sensitivity of detection refers to the detectable limit of concentration of carbon monoxide. Sensors having high sensitivity of detection have a lower detectable limit of concentration, whereas those having low sensitivity of detection have a higher detectable limit of concentration. The sensitivity of detection can be adjusted by utilizing the fact that the output voltage characteristic of the carbon monoxide sensor depends upon the type of catalyst. Compared with carbon monoxide sensors using platinum as a catalyst of electrodes, those using platinum-ruthenium alloy as a catalyst of electrodes generally have lower sensitivity of detection.

Figure 9:
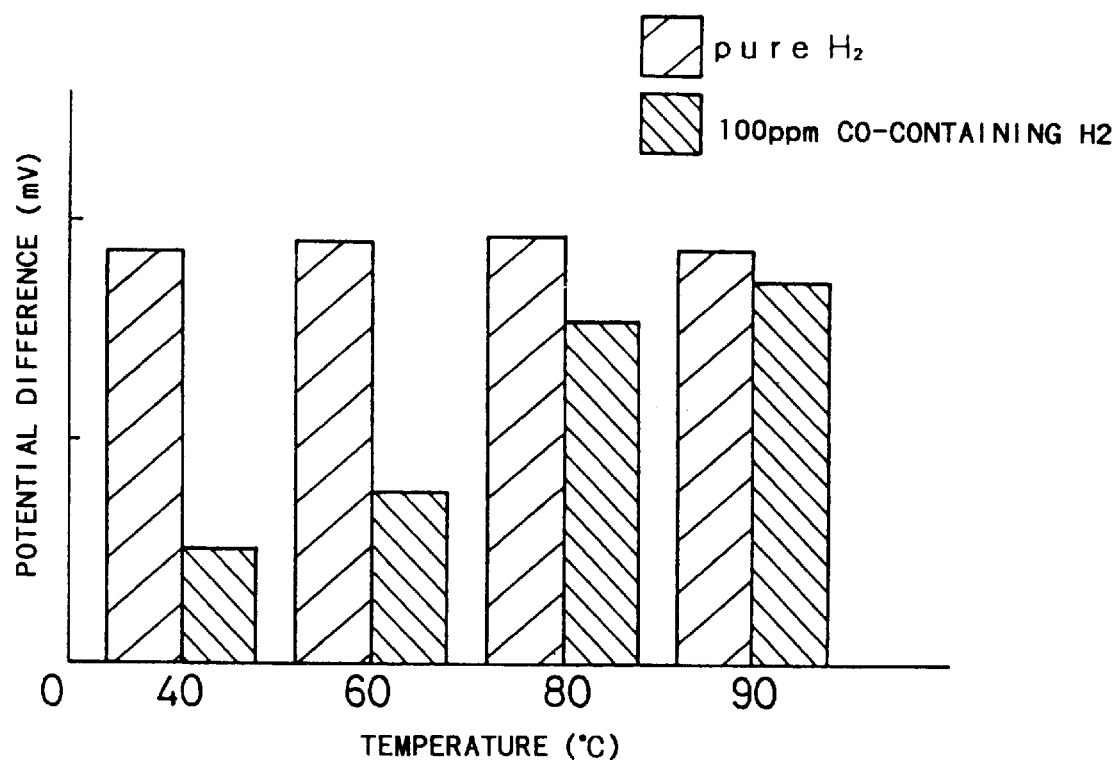
FIG. 9 is a graph showing a relationship between the temperature of the carbon monoxide sensor 1 of the first embodiment and the potential difference.

Alternatively, the sensitivity of detection may be adjusted by taking advantage of the fact that the temperature of the carbon monoxide sensor varies the sensitivity of detection. Since the carbon monoxide sensors of the above embodiments have temperature dependence as described above, the sensitivity of detection can be adjusted by heating or cooling the carbon monoxide sensor. FIG. 9 is a graph showing a relationship between the temperature of the carbon monoxide sensor 1 of the first embodiment and the output voltage (potential difference). This graph clearly shows that the potential difference is significantly varied by the temperature of the carbon monoxide sensor 1. A concrete structure of adjusting the sensitivity of detection with the variation in temperature of a carbon monoxide sensor is given below.

Figure 10:
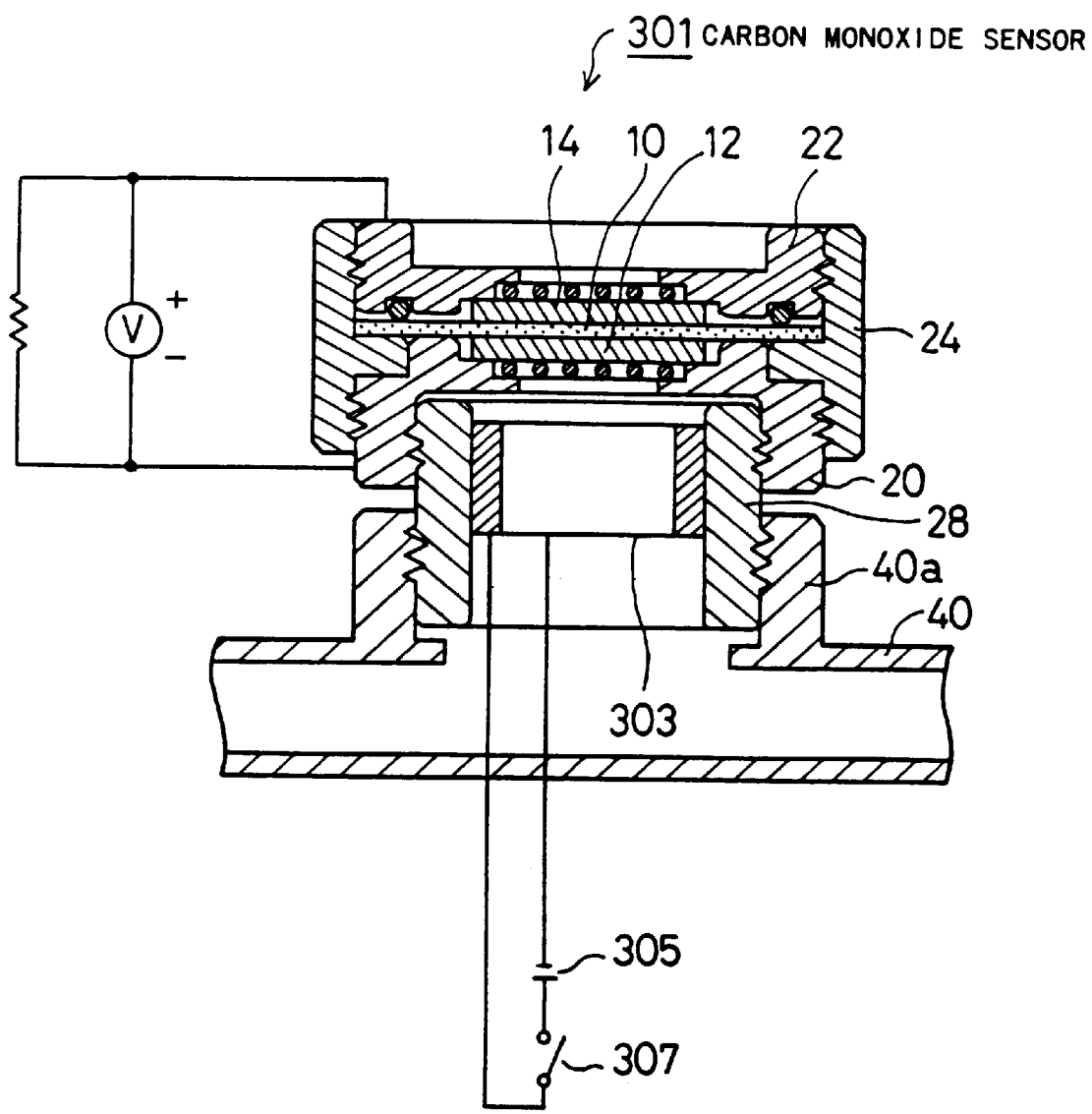
FIG. 10 is a vertical cross sectional view schematically illustrating a carbon monoxide sensor 301 as a fourth embodiment according to the invention.

FIG. 10 is a vertical cross sectional view illustrating a carbon monoxide sensor 301 as a fourth embodiment according to the invention. The carbon monoxide sensor 301 has similar structure to that of the carbon monoxide sensor 1 of the first embodiment, except that a heater 303 is disposed in the gas flow conduit 28. The heater 303 is connected to a circuit including a secondary cell 305 and a switch 307. A control system (not shown) gives instructions to on and off the switch 307 and control the temperature of the carbon monoxide sensor 301, or at least the electrodes 12, to a preset level (for example, 80° C.).

A cylindrical PTC heater is used for the heater 303 in this embodiment, although any other heating elements, such as nichrome wire and carbon-resistant heating elements may also be applicable.

In the carbon monoxide sensor 301 thus constructed, the heater 303 increases the temperature of the carbon monoxide sensor 301, thereby enhancing the anti-poisoning properties of platinum catalyst. This structure including the heater 303 allows the sensitivity of detection to be set lower than that of the structure without any heater.

The temperature of the carbon monoxide sensor without a heater is substantially equal to the temperature of operation, which is approximately 80° C. The preset level of temperature controlled through the on-off operation of the heater 303 is accordingly set to be higher than 80° C. for the lower sensitivity of detection.

In the carbon monoxide sensor 301 of this fourth embodiment, an excessive increase in temperature of the electrode 12-electrolyte membrane 10-electrode 14 structure excessively dries the electrolyte membrane 10 and undesirably heightens the internal resistance. It is thus preferable that the preset level of temperature is not higher than 100° C. Under the condition that the object gas or gaseous fuel on the anode's side is pressurized and sufficiently moistened, however, the electrolyte membrane 10 does not excessively dry even at the temperature of higher than 100° C. The preset level of temperature controlled by the on-off operations of the heater 303 is thus set in an individual carbon monoxide sensor 301 by considering the position of the carbon monoxide sensor 301, the required range of measurement for the concentration of carbon monoxide, and the temperature, pressure, humidity of the gaseous fuel fed to the anode.

Although the heater 303 is disposed on the side exposed to the gaseous fuel relative to the electrolyte membrane 10 in this embodiment, a heater may be placed on the side exposed to the atmosphere. Since the temperature of the atmosphere is generally higher than the temperature of the gaseous fuel or object gas, the heater arranged on the side of the electrode 14 exposed to the atmosphere requires a greater energy for maintaining the carbon monoxide sensor at a predetermined temperature.

In the structure of the fourth embodiment, the sensitivity of detection of the carbon monoxide sensor 301 is lowered by increasing the temperature of the carbon monoxide sensor 301 with the heater 303. The sensitivity of detection of the carbon monoxide sensor can be heightened, on the contrary, by making part of coolant in the stack of fuel cells 210 flow around the carbon monoxide sensor to lower the temperature of the carbon monoxide sensor. In accordance with a concrete structure (not illustrated), a flow path is set in the insulating member 24 and part of coolant in the stack of fuel cells 210 is led into the flow path.

Another carbon monoxide sensor having a modified structure (not illustrated) is given as a fifth embodiment according to the present invention. The structure of the fifth embodiment prevents the catalyst component of the electrode 12 exposed to the gaseous fuel or object gas from being poisoned by carbon monoxide of unexpectedly high concentration. This effectively maintains the performance of the carbon monoxide sensor. The structure of the fifth embodiment is similar to that of the carbon monoxide sensor 301 of the fourth embodiment, except that the carbon monoxide sensor of the fifth embodiment is set at higher temperatures of 140° C. through 160° C.

The increased temperature of the carbon monoxide sensor to 140° C. through 160° C. releases the adsorbed carbon monoxide from the surface of platinum catalyst in the electrode 12, thereby recovering the catalytic activities. Heating by the heater 303 may continue for about one minute after the temperature of the carbon monoxide sensor is increased to 140° C. through 160° C.

In a fuel cell generator system including such a carbon monoxide sensor, the heater 303 is activated at one or a combination of the following timings:

(1) at predetermined intervals during the operation of the fuel cell generator system;

(2) at every activation of the fuel cell generator system;

(3) at every stop of the fuel cell generator system; and (4) at every time when the carbon monoxide sensor detects the extremely high concentration of carbon monoxide greater than a predetermined level.

The structure of the fifth embodiment activates the heater 303 to set the carbon monoxide sensor at high temperatures. This allows carbon monoxide adsorbed by the catalyst in the electrode 12 to be released, thereby recovering the catalytic activities and preventing the performance of the carbon monoxide sensor from being deteriorated.

The carbon monoxide sensor 1, 101, or 301 is arranged in the middle of the gaseous fuel supply conduit 218 as described in the third embodiment above, but may alternatively be arranged in the middle of the gaseous fuel discharge conduit 220. The latter structure can measure the concentration of carbon monoxide included in a gaseous discharge from the stack of fuel cells 210. The carbon monoxide sensors 1, 101, and 301 in the above embodiments are not only used to measure the concentration of carbon monoxide included in the gaseous fuel fed to the fuel cells, but may be applicable to any reactant gas containing hydrogen. All the methanol sensors described later can also be applied to any hydrogen-containing reactant gas.

Sixth through tenth embodiments according to the invention described below are related to the apparatus for detecting an organic compound and the apparatus for detecting a lower alcohol.

Figure 11:
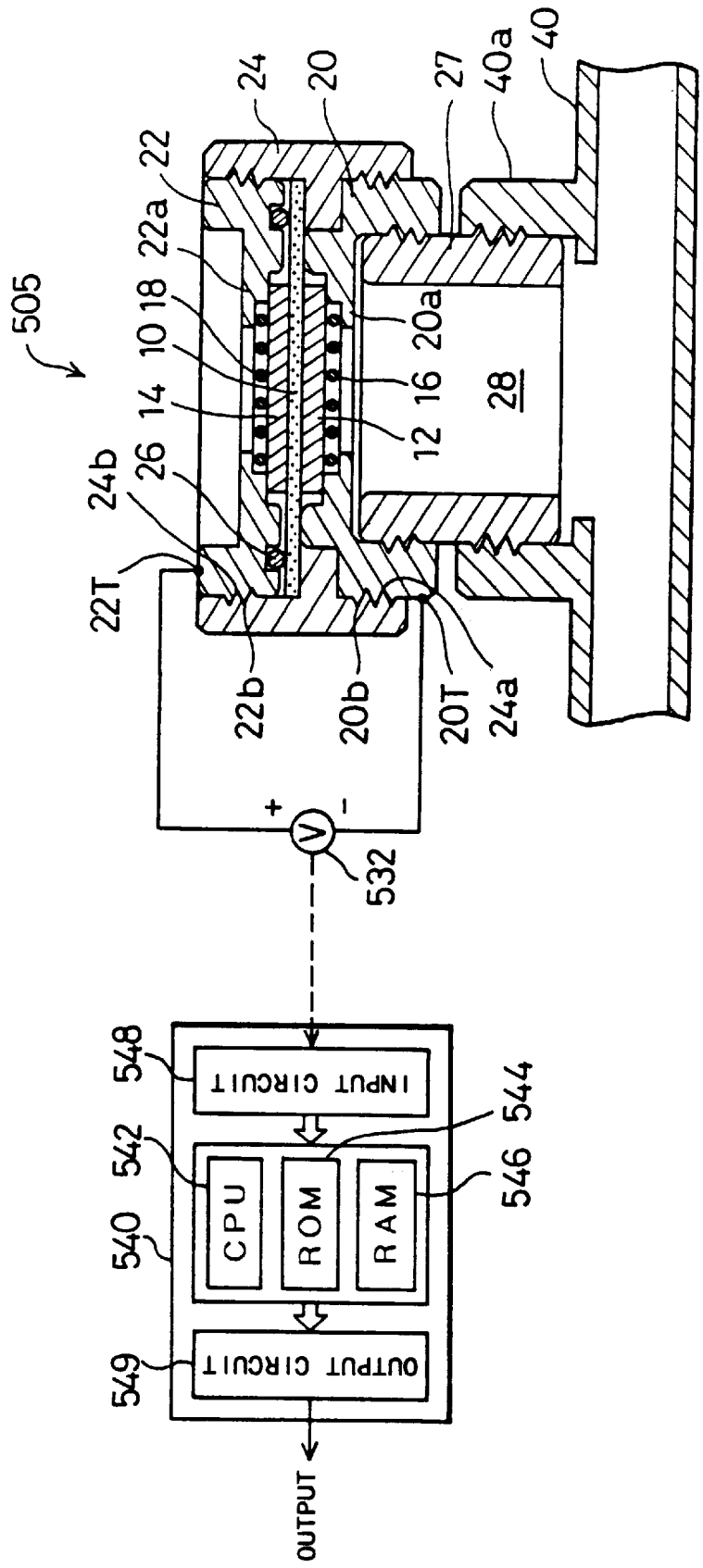
FIG. 11 schematically shows structure of an apparatus 501 for measuring the concentration of methanol with a methanol sensor 505 as a sixth embodiment according to the invention.

FIG. 11 schematically shows structure of an apparatus 501 for measuring the concentration of methanol with a methanol sensor 505 as a sixth embodiment according to the invention. The methanol concentration-measuring apparatus 501 includes a methanol sensor 505, which corresponds to the apparatus for detecting an organic compound and the apparatus for detecting a lower alcohol according to the invention, and an electronic control unit 540.

A primary portion of the methanol sensor 505 is identical with that of the carbon monoxide sensor 1 of the first embodiment. In the structure of the methanol sensor 505 of the sixth embodiment, like numerals denote like elements of the carbon monoxide sensor 1 of the first embodiment, whose explanation is omitted here.

Referring to FIG. 11, the methanol sensor 505 is provided with a voltmeter 532, which is electrically connected to the detection terminals 20T and 22T of the holders 20 and 22 and measures an electromotive force or potential difference between the electrodes 12 and 14. The voltmeter 532 is connected to the electronic control unit 540, which receives output signals from the voltmeter 532. Connection of the voltmeter 532 is determined to give negative polarity to the detection terminal 20T of the holder 20 on the side of the electrode 12 exposed to the gaseous fuel and positive polarity to the detection terminal 22T of the holder 22 on the side of the electrode 14 exposed to the atmosphere.

The electronic control unit 540 is constructed as a logic circuit with a microcomputer. According to a concrete structure, the electronic control unit 540 includes: a CPU 542 for executing a variety of operations according to preset control programs; a ROM 544, in which control programs and control data required for the execution of various operations by the CPU 542 are previously stored; a RAM 546, which various data required for the execution of various operations by the CPU 542 are temporarily written in and read from; an input circuit 548 for receiving output signals from the voltmeter 532 of the methanol sensor 505; and an output circuit 549 for outputting the concentration of methanol included in the gaseous fuel as a linear signal, based on the result of operations by the CPU 542.

The following description regards the process of determining the concentration of methanol included in the hydrogen-rich gaseous fuel by the methanol concentration-measuring apparatus 501 thus constructed. A supply of gaseous hydrogen included in the hydrogen-rich gaseous fuel is fed to the electrode 12 of the methanol sensor 505, while a supply of oxygen included in the atmosphere is fed to the electrode 14. The reactions expressed by Equations (6) and (7) above accordingly proceed on the surface of the electrodes 12 and 14 across the electrolyte membrane 10.

These reactions are identical with those in a fuel cell, which uses hydrogen and oxygen as fuels to generate electrical energy. An electromotive force is thus generated between the electrodes 12 and 14. An electromotive force generated under the condition that no load is placed between the electrodes 12 and 14 is referred to as an open circuit voltage OCV or no-load voltage. In case that methanol exists in the gaseous fuel, the open circuit voltage OCV generated between the electrodes 12 and 14 decreases with an increase in concentration of methanol included in the gaseous fuel. This phenomenon is ascribed to the fact that methanol included in the gaseous fuel passes through the electrolyte membrane 10 and reacts with oxygen on the surface of the electrode 14 in contact with the electrolyte membrane 10, thereby lowering the potential on the electrode 14.

Figure 12:
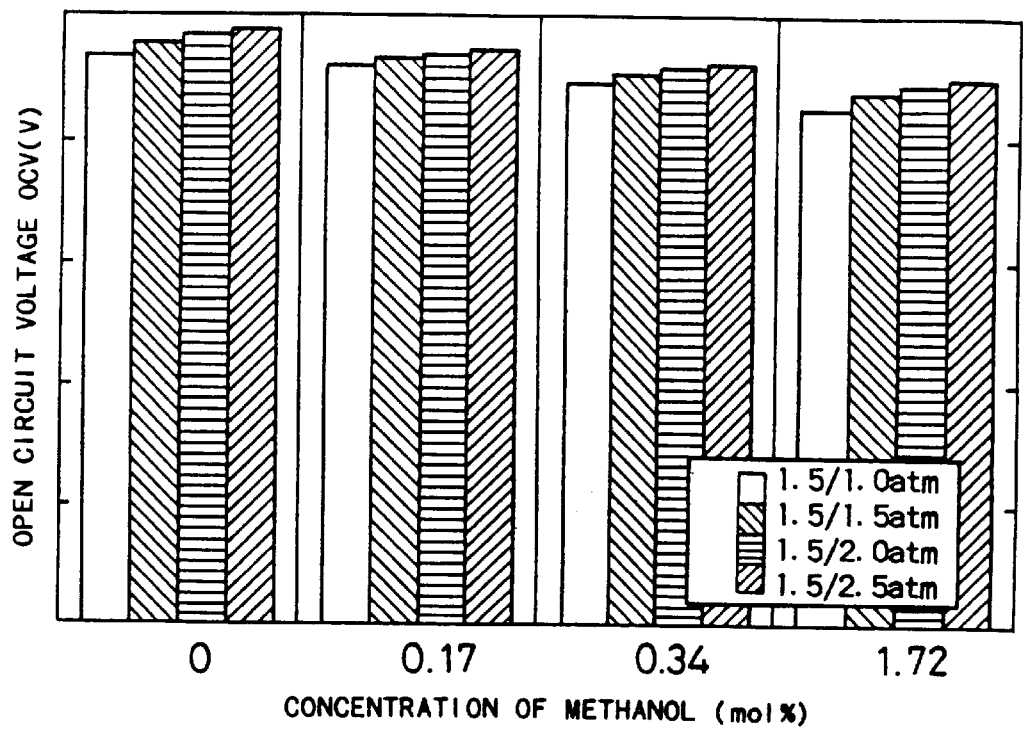
FIG. 12 is a graph showing a relationship between the concentration of methanol included in the gaseous fuel and the open circuit voltage OCV generated between the electrodes 12 and 14.

FIG. 12 is a graph showing a relationship between the concentration of methanol included in the gaseous fuel and the open circuit voltage OCV generated between the electrodes 12 and 14. Non-hatched and three hatched bars in the graph respectively represent open circuit voltages OCV at respective concentrations of methanol under the conditions that the electrode 14 is exposed to an oxygen-containing gas containing the air of 1.0 atm. (101 kPa), 1.5 atm. (152 kPa), 2.0 atm. (203 kPa), or 2.5 atm. (253 kPa) with respect to the gaseous fuel of 1.5 atm. (152 kPa). These conditions are also shown in the lower right box of FIG. 12. The graph of FIG. 12 clearly shows that the open circuit voltage OCV gradually decreases with an increase in concentration of methanol included in the gaseous fuel under any of the four conditions.

Figure 13:
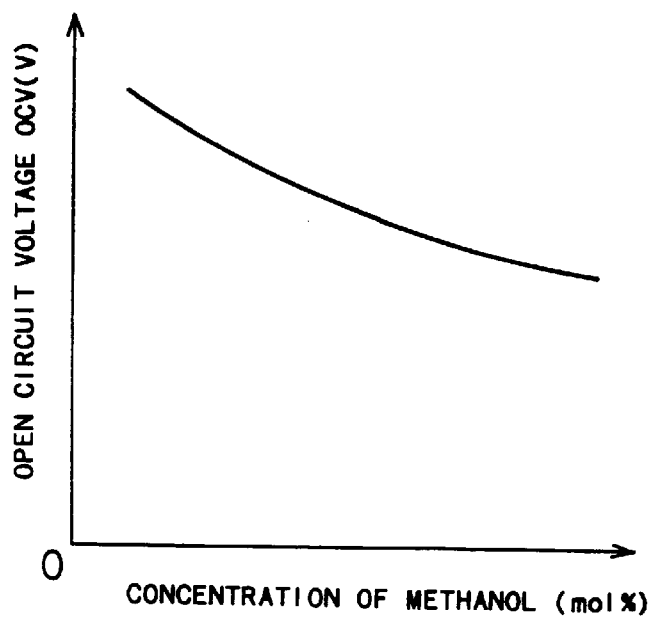
FIG. 13 is a graph showing a relationship between the concentration of methanol included in the gaseous fuel and the open circuit voltage OCV measured by the voltmeter 532.

In the methanol concentration-measuring apparatus 501 of the sixth embodiment, the voltmeter 532 measures the open circuit voltage OCV and transmits a detection signal representing the open circuit voltage OCV via the input circuit 548 into the electronic control unit 540. The CPU 542 of the electronic control unit 540 refers to a map previously stored in the ROM 544 and representing a relationship between the concentration of methanol included in the gaseous fuel and the open circuit voltage OCV measured by the voltmeter 532, for example, a map as shown in FIG. 13, determines the concentration of methanol corresponding to the input open circuit voltage OCV, and outputs the concentration of methanol via the output circuit 549.

The methanol concentration-measuring apparatus 501 of this embodiment can determine the concentration of methanol included in the hydrogen-rich gas with high precision.

In the methanol sensor 505, while one electrode 12 receives a supply of gaseous fuel, the other electrode 14 is exposed to the atmosphere. This does not require any specific gas supply conduit on the electrode 14, thereby reducing the size of the whole methanol sensor 505.

In the methanol concentration-measuring apparatus 501 of the six embodiment, the CPU 542 reads the open circuit voltage OCV measured by the voltmeter 532 via the input circuit 548, determines the concentration of methanol included in the gaseous fuel by referring to the map previously stored in the ROM 544 (for example, the map shown in FIG. 13), and outputs the concentration of methanol via the output circuit 549. According to another possible structure, the open circuit voltage OCV measured by the voltmeter 532 is compared with a preset value. When the measured open circuit voltage OCV is smaller than the preset value, the CPU 542 outputs a predetermined signal showing that the gaseous fuel contains methanol of not less than a predetermined concentration. For example, the open circuit voltage OCV measured by the voltmeter 532 is compared with a preset value previously stored in the ROM 544 of the electronic control unit 540. The output circuit 549 generates an L-level signal for the open circuit voltage OCV of greater than the preset value and an H-level signal for the open circuit voltage OCV of not greater than the preset value. The preset value depends upon the characteristics of equipment to which the methanol concentration-measuring apparatus 501 is attached, and is set corresponding to the minimum concentration of methanol to be detected. It is preferable that the voltmeter 532 has a sufficiently high internal impedance not to affect the open circuit voltage OCV.

Figure 14:
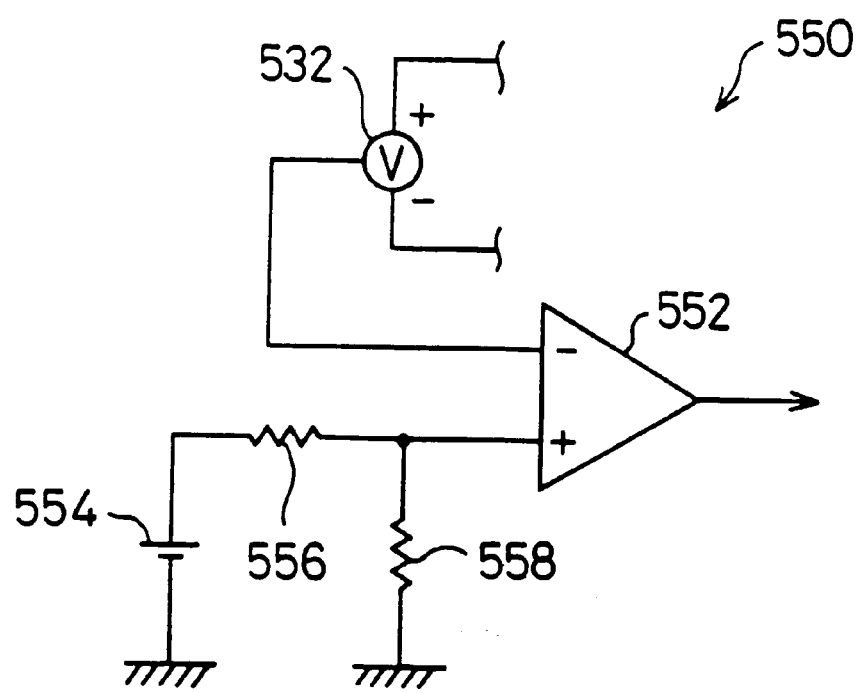
FIG. 14 is a circuit diagram showing a determination circuit 550 applicable in place of the electronic control unit 540 of FIG. 11.

In accordance with another preferable structure, the electronic control unit 540 may be replaced by a determination circuit 550 shown in FIG. 14. The determination circuit 550 includes a comparator 552, a power source 554 for applying a predetermined constant voltage to a plus input terminal of the comparator 552, and first and second resistors 556 and 558. A minus input terminal of the comparator 552 is connected to the voltmeter 532 and receives an output signal from the voltmeter 532. The output voltage of the voltmeter 532 decreases with an increase in concentration of methanol included in the gaseous fuel. The first and the second resistors 556 and 558 are thus set to make the predetermined constant voltage applied to the plus input terminal of the comparator 552 equal to the voltage of the output signal from the voltmeter 532 when the concentration of methanol in the gaseous fuel is equal to a preset value (for example, 3 mol %). This setting allows the output of the comparator 552 to be varied depending upon whether the concentration of methanol in the gaseous fuel is greater or less than the preset value. When the concentration of methanol is less than the preset value, a voltage higher than a reference voltage is input into the minus input terminal of the comparator 552, and an L-level signal is thereby output from the output terminal of the comparator 552. When the concentration of methanol is greater than the preset value, on the contrary, a voltage lower than the reference voltage is input into the minus input terminal of the comparator 552, and an H-level signal is thereby output from the output terminal of the comparator 552.

A methanol concentration-measuring apparatus including the determination circuit 550 in place of the electronic control unit 540 has a simpler structure but effectively informs the user that the concentration of methanol included in the gaseous fuel is not less than a preset value.

The methanol concentration-measuring apparatus 501 has temperature dependence like the carbon monoxide sensor 1 of the first embodiment; that is, the output voltage for a fixed concentration of methanol is varied depending upon the temperature of the methanol sensor 505. A preferable structure thus previously determines temperature-output voltage and methanol concentration-output voltage characteristics, and corrects the output voltage based on the temperature of the methanol sensor 505 for determining the concentration of methanol with further enhanced precision.

Figure 15:
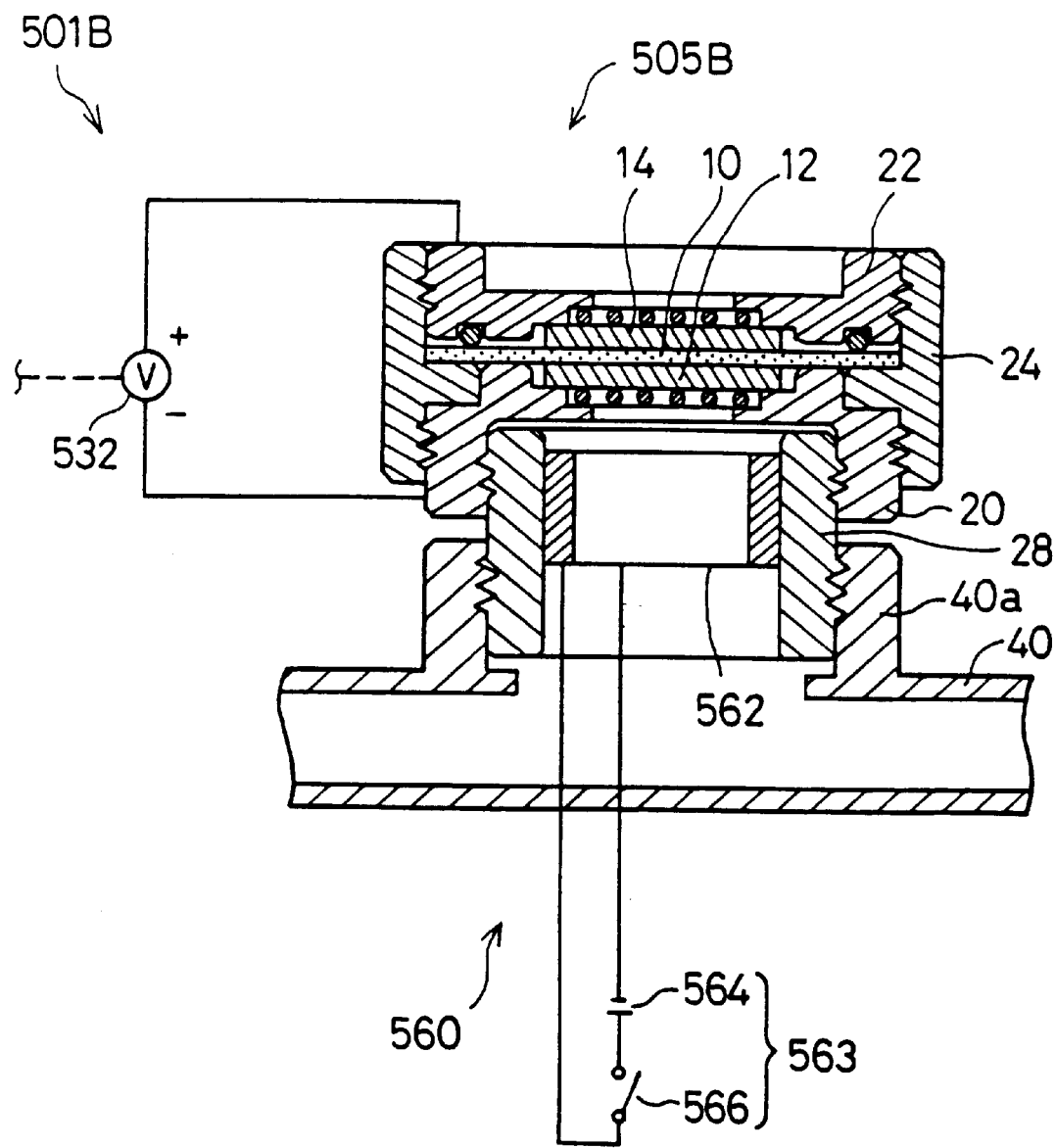
FIG. 15 schematically illustrates structure of a methanol sensor 505B incorporated in another methanol concentration-measuring apparatus 501B as a seventh embodiment according to the invention.

Another methanol concentration-measuring apparatus 501B developed for the purpose of determining the concentration of methanol with higher precision by taking account of the temperature dependence is given as a seventh embodiment according to the invention. FIG. 15 schematically illustrates structure of a methanol sensor 505B incorporated in the methanol concentration-measuring apparatus 501B of the seventh embodiment. The methanol concentration-measuring apparatus 501B of the seventh embodiment has similar structure to that of the methanol concentration-measuring apparatus 501 of the sixth embodiment, except that the methanol concentration-measuring apparatus 501B further includes a temperature control mechanism 560 for controlling the temperature of the methanol sensor 505B. In the structure of the methanol concentration-measuring apparatus 501B of the seventh embodiment, like numerals denote like elements of the methanol concentration-measuring apparatus 501 of the sixth embodiment, whose explanation is omitted here. The methanol sensor 505B of the seventh embodiment also has structure corresponding to that of the carbon monoxide sensor 301 of the fourth embodiment shown in FIG. 10.

The temperature control mechanism 560 incorporated in the methanol sensor 505B includes a heater 562 arranged in the gas flow conduit 28 and a control circuit 563 connected to the heater 562. The control circuit 563 further includes a power source 564 and a switch 566. The temperature control mechanism 560 receives instructions from a control system (not shown) to on and off the switch 566 and controls the temperature of the methanol sensor 505B, or at least the electrolyte membrane 10 and the electrodes 12 and 14, to a preset level (for example, 80° C.). An excessive increase in temperature of the electrode 12-electrolyte membrane 10-electrode 14 structure excessively dries the electrolyte membrane 10 and undesirably heightens the internal resistance. It is thus preferable that the preset level is not higher than 100° C. Under the condition that the object gas or gaseous fuel on the anode's side is pressurized and sufficiently moistened, however, the electrolyte membrane 10 does not excessively dry even at the temperature of higher than 100° C.

A cylindrical PTC heater is used for the heater 562 in this embodiment, although any other heating elements, such as nichrome wire and carbon-resistant heating elements, may also be applicable.

In the methanol concentration-measuring apparatus 501B of the seventh embodiment, the temperature of the methanol sensor 505B is controlled to a preset level by means of the heater 562. This structure allows the reactions expressed by Equations (6) and (7) given above to proceed in a constant state on the electrodes 12 and 14, and allows methanol included in the gaseous fuel and passing through the electrolyte membrane 10 to react in a constant state on the electrode 14. The structure of the seventh embodiment thus determines the concentration of methanol included in the gaseous fuel with high precision.

Like the methanol concentration-measuring apparatus 501 of the sixth embodiment, the methanol concentration-measuring apparatus 501B of the seventh embodiment may include the determination circuit 550 in place of the electronic control unit 540.

Although the temperature control mechanism 560 is disposed in the gas flow conduit 28 of the gaseous fuel in the methanol concentration-measuring apparatus 501B of the seventh embodiment, the temperature control mechanism 560 may be placed on the opposite side exposed to the atmosphere relative to the electrolyte membrane 10.

Figure 16:
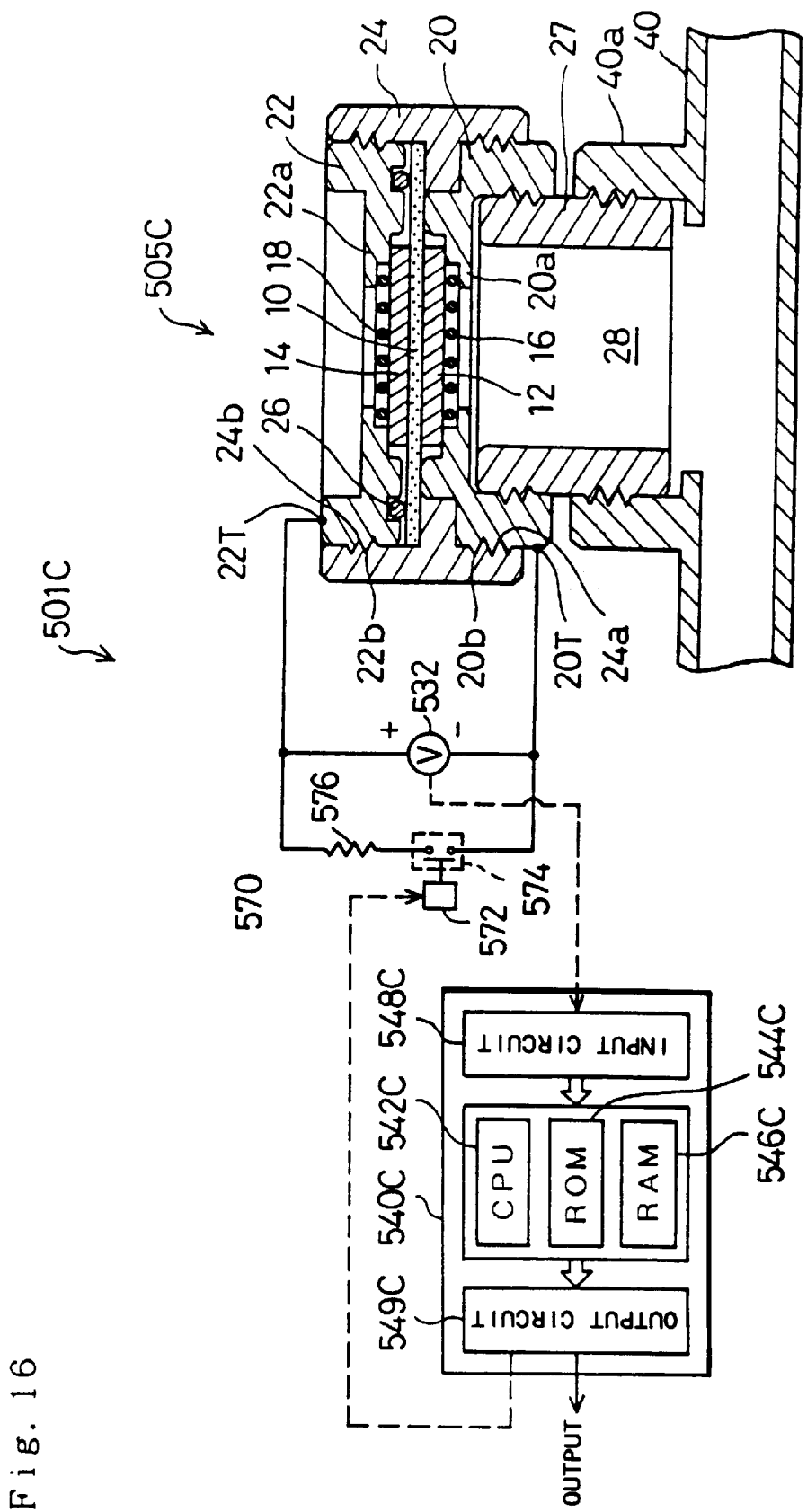
FIG. 16 schematically illustrates structure of still another methanol concentration-measuring apparatus 501C as an eighth embodiment according to the invention.

FIG. 16 schematically illustrates structure of still another methanol concentration-measuring apparatus 501C as an eighth embodiment according to the invention. The methanol concentration-measuring apparatus 501C of the eighth embodiment has similar structure to that of the methanol concentration-measuring apparatus 501 of the sixth embodiment, except that the methanol concentration-measuring apparatus 501C further includes a switching mechanism 570. In the structure of the methanol concentration-measuring apparatus 501C of the eighth embodiment, like numerals denote like elements of the methanol concentration-measuring apparatus 501 of the sixth embodiment, whose explanation is omitted here.

The switching mechanism 570 is incorporated in a methanol sensor 505C of the methanol concentration-measuring apparatus 501C and includes a relay 572, a contact 574 of the relay 572, and a resistor 576. The switching mechanism 570 is arranged in parallel with the voltmeter 532 between the detection terminals 20T and 22T, whereas the contact 574 of the relay 572 and the resistor 576 are disposed in series.

While the relay 572 is off, the contact 574 of the relay 572 is in an open position to disconnect the resistor 576 from the detection terminals 20T and 22T. The potential difference measured by the voltmeter 532 under such a condition corresponds to the open circuit voltage OCV between the electrodes 12 and 14. While the relay 572 is on, on the other hand, the contact 574 of the relay 572 is in a closed position to connect the resistor 576 with the detection terminals 20T and 22T. The potential difference measured by the voltmeter 532 under such a condition corresponds to the potential difference between both terminals of the resistor 576. The relay 572 is further connected to an output circuit 549C of an electronic control unit 540C and is driven and controlled by the electronic control unit 540C. The electronic control unit 540C has identical hardware to that of the electronic control unit 540 of the sixth embodiment.

Operation of the methanol concentration-measuring apparatus 501C of the eighth embodiment is described below. The electronic control unit 540C of the methanol concentration-measuring apparatus 501C outputs on or off signals via the output circuit 549C to the relay 572 at every input of an interruption signal or at predetermined intervals (for example, at every 20 msec).

While the relay 572 is off and the contact 574 of the relay 572 is in the open position, the resistor 576 is disconnected from the detection terminals 20T and 22T, and the potential difference measured by the voltmeter 532 represents the open circuit voltage OCV between the electrodes 12 and 14. Under these conditions, the methanol concentration-measuring apparatus 501C can determine the concentration of methanol included in the gaseous fuel or object gas fed to the gas flow conduit 28, in the same manner as the methanol concentration-measuring apparatus 501 of the sixth embodiment. While the relay 572 is on and the contact 574 of the relay 572 is in the closed position, on the contrary, the resistor 576 is connected to the detection terminals 20T and 22T, and the potential difference measured by the voltmeter 532 represents the potential difference between both terminals of the resistor 576. Under these conditions, the methanol concentration-measuring apparatus 501C can determine the concentration of carbon monoxide included in the gaseous fuel or object gas fed to the gas flow conduit 28, in the same manner as the carbon monoxide sensor 1 of the first embodiment.

In the methanol concentration-measuring apparatus 501C of the eighth embodiment, the voltmeter 532 measures the potential difference between the detection terminals 20T and 22T, that is, the potential difference between both terminals of the resistor 576, in such state that the relay 572 is on to close the contact 574 for measuring carbon monoxide included in the gaseous fuel. A signal representing the measured potential difference is input into the electronic control unit 540C via an input circuit 548C. A CPU 542C of the electronic control unit 540C refers to a map previously stored in a ROM 544C and representing a relationship between the concentration of carbon monoxide included in the gaseous fuel and the potential difference measured by the voltmeter 532, for example, the map as shown in FIG. 2, determines the concentration of carbon monoxide corresponding to the input potential difference, and outputs the concentration of carbon monoxide via the output circuit 549C.

The methanol concentration-measuring apparatus 501C of the eighth embodiment has the switching mechanism 570 of simple structure, which selects either measurement of carbon monoxide or measurement of methanol. The switching mechanism 570 allows both carbon monoxide and methanol included in the gaseous fuel or object gas to be detected with high precision only by simple on-off operations of the relay 572 included in the switching mechanism 570.

Poisoning of the catalyst in the electrode 12 by the effect of carbon monoxide included in the gaseous fuel is temperature dependent as described previously. It is accordingly preferable that the methanol concentration-measuring apparatus 501C of the eighth embodiment further includes the temperature control mechanism 560 of the seventh embodiment shown in FIG. 15, when the temperature of the gaseous fuel or object gas is significantly varied.

Like the methanol concentration-measuring apparatus 501 of the sixth embodiment, in the methanol concentration-measuring apparatus 501C of the eighth embodiment, the electronic control unit 540C reads the potential difference measured by the voltmeter 532, determines the concentration of methanol or the concentration of carbon monoxide included in the gaseous fuel by referring to the map previously stored in the ROM 544C (for example, the map shown in FIG. 13 or FIG. 2), and outputs the concentration of methanol or the concentration of carbon monoxide via the output circuit 549C. According to another possible structure, the potential difference measured by the voltmeter 532 is compared with a preset first potential difference for determination of methanol or a preset second potential difference for determination of carbon monoxide. When the measured potential difference is less than the preset first or second potential difference, the electronic control unit 540C outputs a predetermined first signal showing that the gaseous fuel contains methanol of not less than a predetermined first concentration or a predetermined second signal showing that the gaseous fuel contains carbon monoxide of not less than a predetermined second concentration. For example, the potential difference measured by the voltmeter 532 is compared with a preset first value for determination of methanol or a preset second value for determination of carbon monoxide previously stored in the ROM 544C of the electronic control unit 540C. The output circuit 549C generates an L-level signal for the potential difference of greater than the preset first or second value and an H-level signal for the potential difference of not greater than the preset first or second value. Another preferable structure includes two determination circuits 550 shown in FIG. 14, one for determination of methanol and the other for determination of carbon monoxide, in place of the electronic control unit 540C. Reference voltages used in the respective determination circuits are set according to the characteristics of the respective potential differences.

Figure 17:
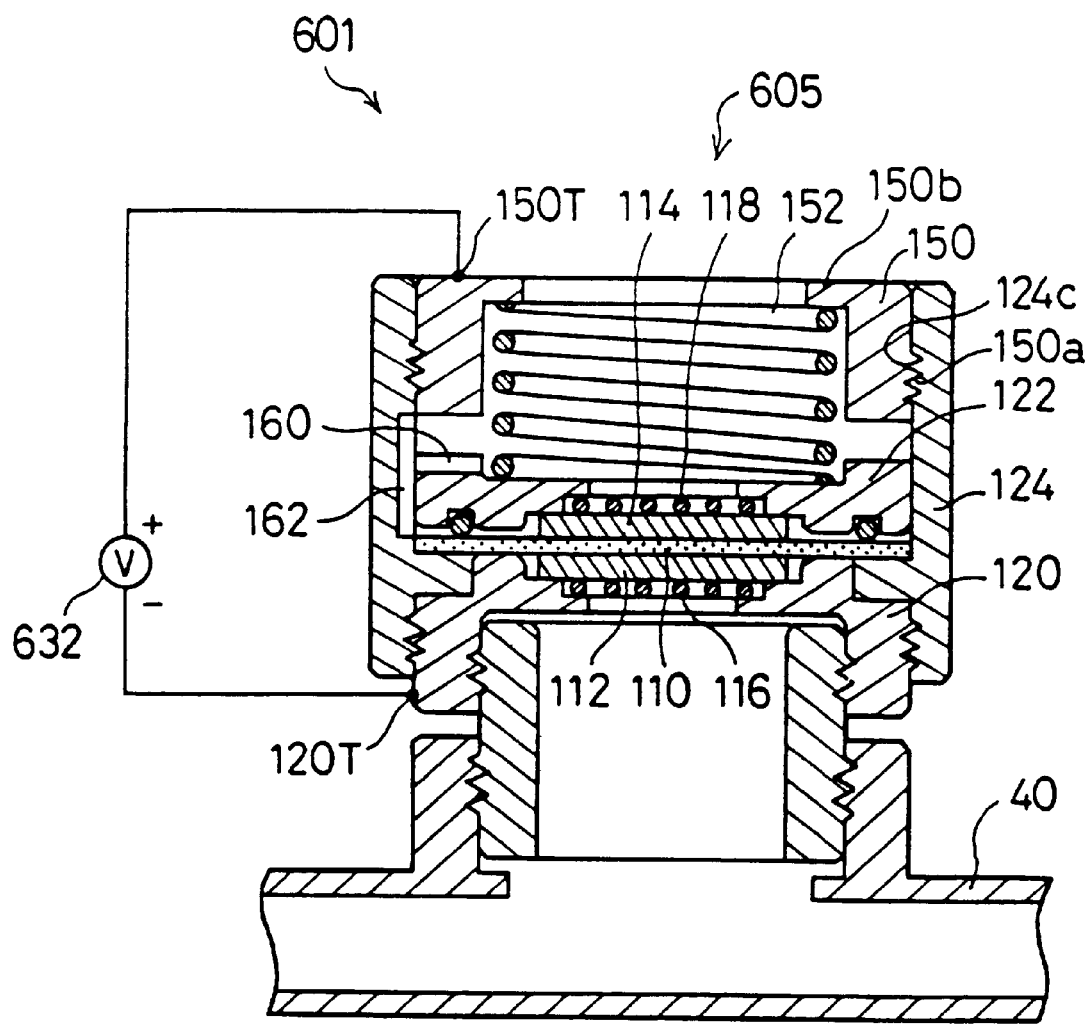
FIG. 17 schematically illustrates structure of a methanol sensor 605 incorporated in another methanol concentration-measuring apparatus 601 as a ninth embodiment according to the invention.

FIG. 17 schematically illustrates structure of a methanol sensor 605 incorporated in another methanol concentration-measuring apparatus 601 as a ninth embodiment according to the invention. A primary portion of the methanol sensor 605 is identical with that of the carbon monoxide sensor 101 of the second embodiment shown in FIG. 3. In the structure of the methanol sensor 605 of the ninth embodiment, like numerals denote like elements of the carbon monoxide sensor 101 of the second embodiment, whose explanation is omitted here.

Referring to FIG. 17, the methanol sensor 605 is provided with a voltmeter 632, which is electrically connected to the detection terminals 120T and 150T of the holders 120 and 150 and measures an electromotive force or potential difference between the electrodes 112 and 114. Connection of the voltmeter 632 is determined to give negative polarity to the detection terminal 120T of the lower holder 120 on the side of the electrode 112 exposed to the gaseous fuel and positive polarity to the detection terminal 150T of the third holder 150 on the side of the electrode 114 exposed to the atmosphere. This configuration of the voltmeter 632 is similar to that of the voltmeter 532 in the methanol sensor 505 of the sixth embodiment. The voltmeter 632 measures the open circuit voltage OCV generated between the electrodes 112 and 114.

Like the carbon monoxide sensor 101 of the second embodiment, when the pressure of gaseous fuel or object gas abnormally increases, the methanol sensor 605 of the ninth embodiment releases the heightened pressure to the atmosphere, thus effectively canceling the abnormal increase of gas pressure which may cause some troubles or problems. The methanol sensor 605 measures the open circuit voltage OCV generated between the electrodes 112 and 114 by means of the voltmeter 632, and thereby determines the concentration of methanol included in the object as with high precision, in the same manner as the methanol sensor 505 of the sixth embodiment.

Like the carbon monoxide sensor 101 of the second embodiment, in the methanol concentration-measuring apparatus 601 of the ninth embodiment, the voltage=0 [V] measured by the voltmeter 132 implies an operation of safety valve function to release the abnormally heightened gas pressure to the atmosphere.

According to another possible structure, an impedance between the detection terminal 120T of the lower holder 120 and the detection terminal 150T of the third holder 150 is measured. In this modified structure, infinite impedance implies an operation of safety valve function, and a signal representing an operation of safety valve function is output to the control system.

Figure 18:
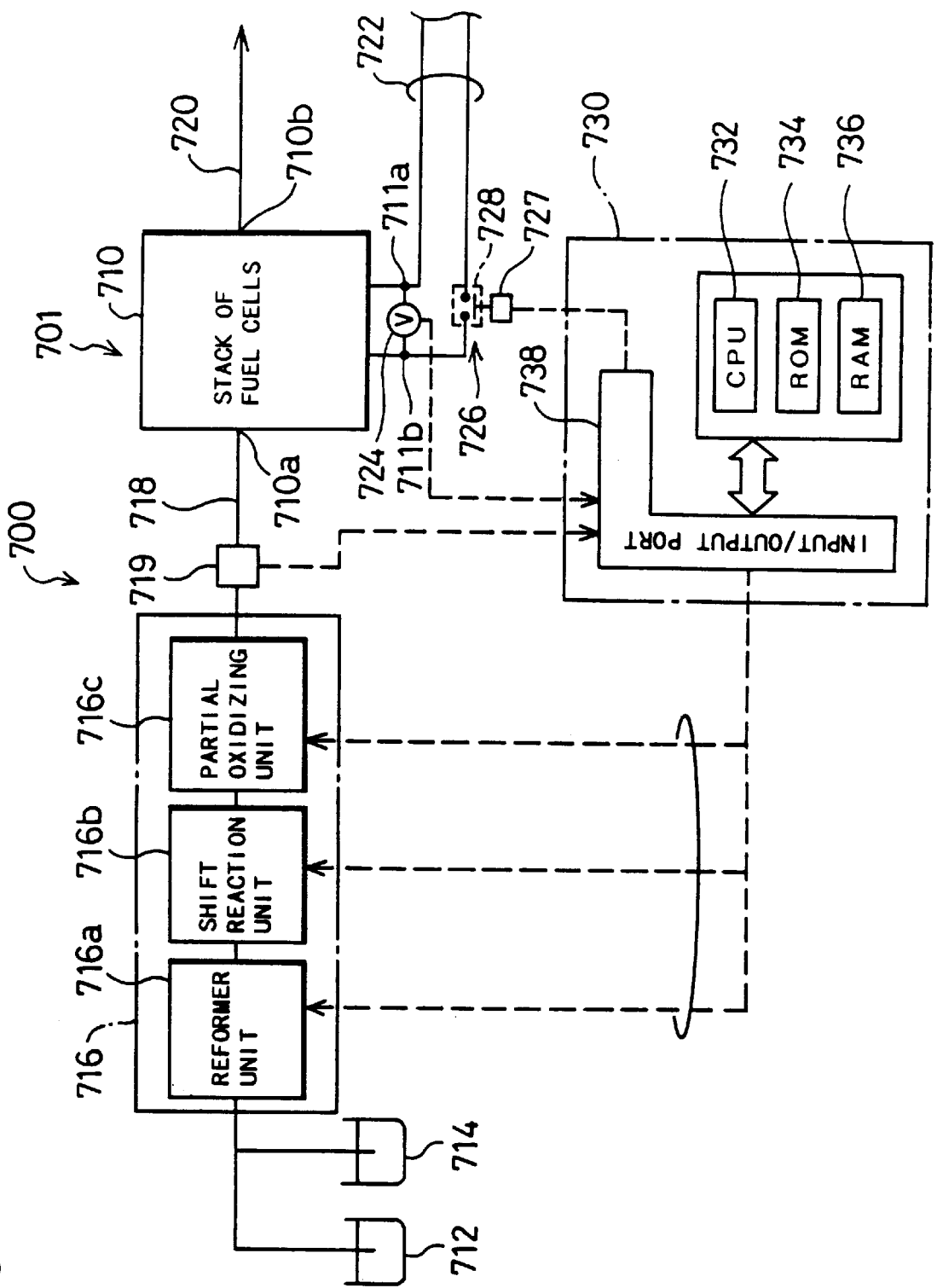
FIG. 18 is a block diagram schematically illustrating structure of a fuel cell generator system 700 with a methanol concentration-measuring apparatus 701 as a tenth embodiment according to the invention.

FIG. 18 is a block diagram schematically illustrating structure of a fuel cell generator system 700 with a methanol concentration-measuring apparatus 701 as a tenth embodiment according to the invention. The fuel cell generator system 700 includes a stack of polymer electrolyte fuel cells 710 for generating electrical energy, a reformer 716 for generating hydrogen-rich gas from methanol stored in a methanol reservoir 712 and water stored in a water reservoir 714, a gaseous fuel supply conduit 718 for feeding the hydrogen-rich gas generated by the reformer 716 as a gaseous fuel to the stack of fuel cells 710, and a gaseous fuel discharge conduit 720 for discharging the residual gas from the stack of fuel cells 710. The fuel cell generator system 700 further includes a voltmeter 724 for measuring a potential difference between output terminals 711a and 711b of the stack of fuel cells 710, a cut-off mechanism 726 disposed in the course of a conductive line 722, and a carbon monoxide sensor 719 arranged in the middle of the gaseous fuel supply conduit 718. The conductive line 722 connects the output terminals 711a and 711b of the stack of fuel cells 710 with a driving apparatus (not shown) driven by means of outputs from the fuel cell generator system 700.

Figure 19:
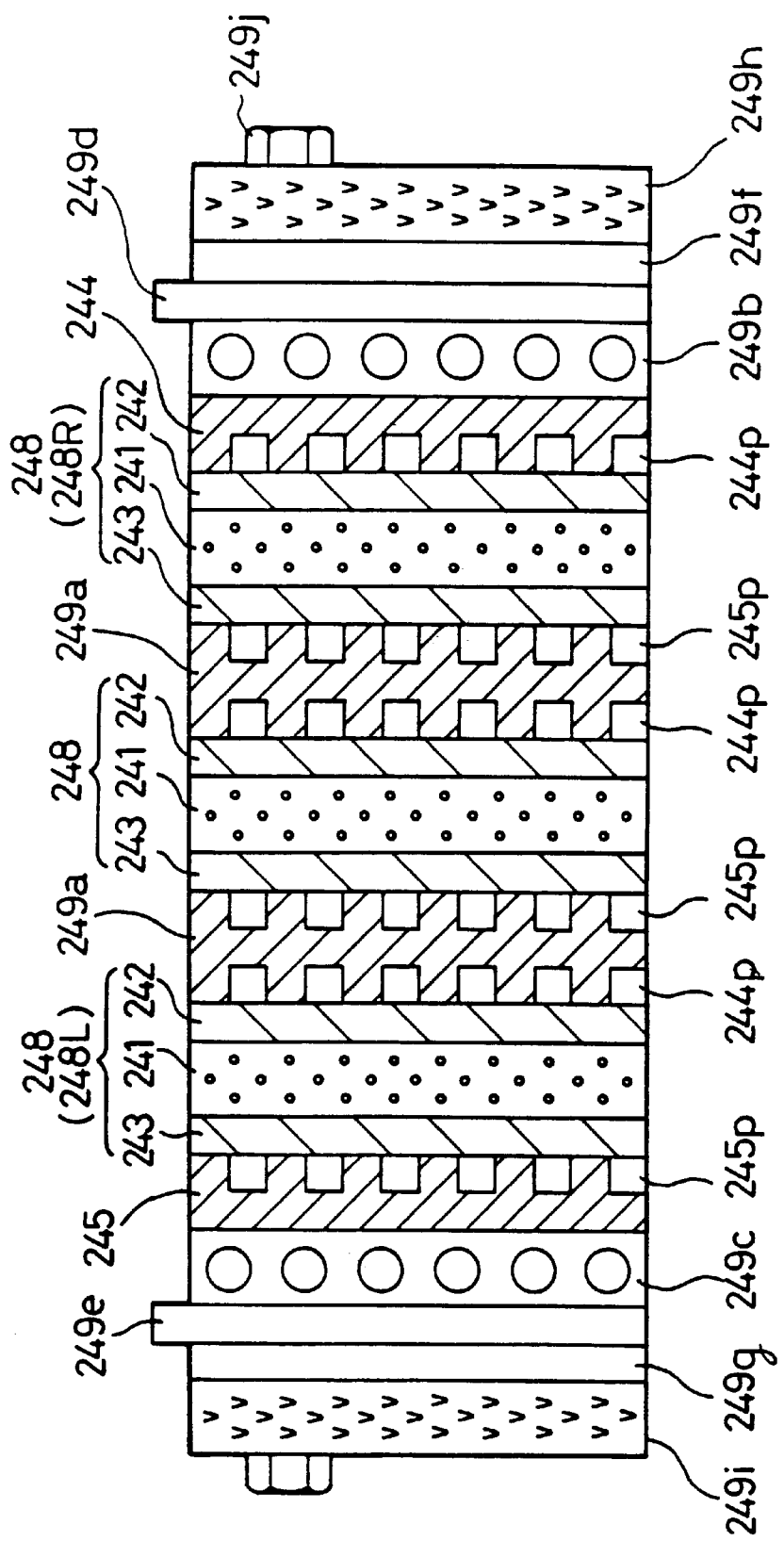
FIG. 19 schematically illustrates a typical structure of the stack of fuel cells 710

The stack of fuel cells 710 has similar structure to that of the stack of fuel cells 210 incorporated in the fuel cell generator system 200 of the third embodiment. FIG. 19 schematically illustrates a typical structure of the stack of fuel cells 710, which includes a plurality of layer units 248, which are laid one upon another via separators 249a. Each layer unit 248 includes an anode 242, an electrolyte membrane 241, and a cathode 243 as shown in FIG. 7. The separator 249a is composed of the same material as the first separator 244 and the second separator 245 of the unit fuel cell shown in FIG. 7. The separator 249a is combined with the surface of the anode 242 of one adjacent layer unit 248 (on the left in the drawing of FIG. 19) to constitute flow paths 244P for gaseous fuel, while being combined with the surface of the cathode 243 of the other adjacent layer unit 248 (on the right in the drawing of FIG. 19) to constitute flow paths 245P for oxygen-containing gas. A first separator 244 is disposed immediately outside a right-most layer unit 248R in the drawing to constitute only the flow paths 244P for gaseous fuel. A second separator 245 is, on the other hand, disposed immediately outside a left-most layer unit 248L in the drawing to constitute only the flow paths 245P for oxygen-containing gas.

The polymer electrolyte fuel cell 10 further includes: a pair of coolant flow paths 249b and 249c respectively arranged outside the first and the second separators 244 and 245; a pair of current collectors 249d and 249e respectively disposed outside the coolant flow paths 249b and 249c; a pair of end plates 249h and 249i arranged via insulating plates 249f and 249g as outer-most layers to support all the above structural elements; and a pair of clamping bolts 249j for clamping and locking the end plates 249h and 249i.

The output terminals 711a and 711b are attached to the current collectors 249d and 249e of the stack of fuel cells 710 thus constructed.

Referring back to FIG. 18, the gaseous fuel supply conduit 718 connects the reformer 716 with an anode-side gas inlet 710a of the stack of fuel cells 710. According to a concrete structure, the anode-side gas inlet 710a is connected to a manifold (not shown) and further to the plurality of first channels 244p (see FIG. 7) formed for the flows of gaseous fuel in the stack of fuel cells 710 via the manifold. An anode-side gas outlet 710b of the stack of fuel cells 710 is also connected to another manifold (not shown) and further to the plurality of first channels 244p in the stack of fuel cells 710 via the manifold. The direction of connection of the gas outlet 710b is opposite to the direction of connection of the gaseous fuel supply conduit 718.

Like the reformer 216 in the fuel cell generator system 200 of the third embodiment, the reformer 716 includes a reformer unit 716a, a shift reaction unit 716b, and a partial oxidizing unit 716c. The units 716a through 716c of the reformer 716 are respectively connected to an electronic control unit 730.

The cut-off mechanism 726 includes a relay 727 and a contact 728 of the relay 727. While the relay 727 is off, the contact 728 of the relay 727 is in a closed position to connect the output terminals 711a and 711b of the stack of fuel cells 710 with the driving apparatus and transmit outputs from the stack of fuel cells 710 to the driving apparatus. While the relay 727 is on, on the contrary, the contact 728 of the relay 727 is in an open position to disconnect the output terminals 711a and 711b from the driving apparatus. The relay 727 of the cut-off mechanism 726 is further connected to the electronic control unit 730 via a conductive line and activated by a driving signal output from the electronic control unit 730.

The electronic control unit 730 has similar structure to that of the electronic control unit 230 in the fuel cell generator system 200 of the third embodiment. The electronic control unit 730 includes a CPU 732, a ROM 734, a RAM 736, an and an input/output port 738.

In the drawing of FIG. 18, only the gas system on the anode's side is shown and that on the cathode's side is omitted.

The methanol concentration-measuring apparatus 701 includes the stack of fuel cells 710, the voltmeter 724, the cut-off mechanism 726, and the electronic control unit 730. As described previously in the sixth through the ninth embodiments, the essential structure of the methanol sensor according to the present invention is identical with a stack of polymer electrolyte fuel cells. The stack of fuel cells 710 is thus used as a methanol sensor for measuring methanol included in a gaseous fuel. The process of measuring methanol included in the gaseous fuel with the stack of fuel cells 710 functioning as a methanol sensor is described below.

Figure 20:
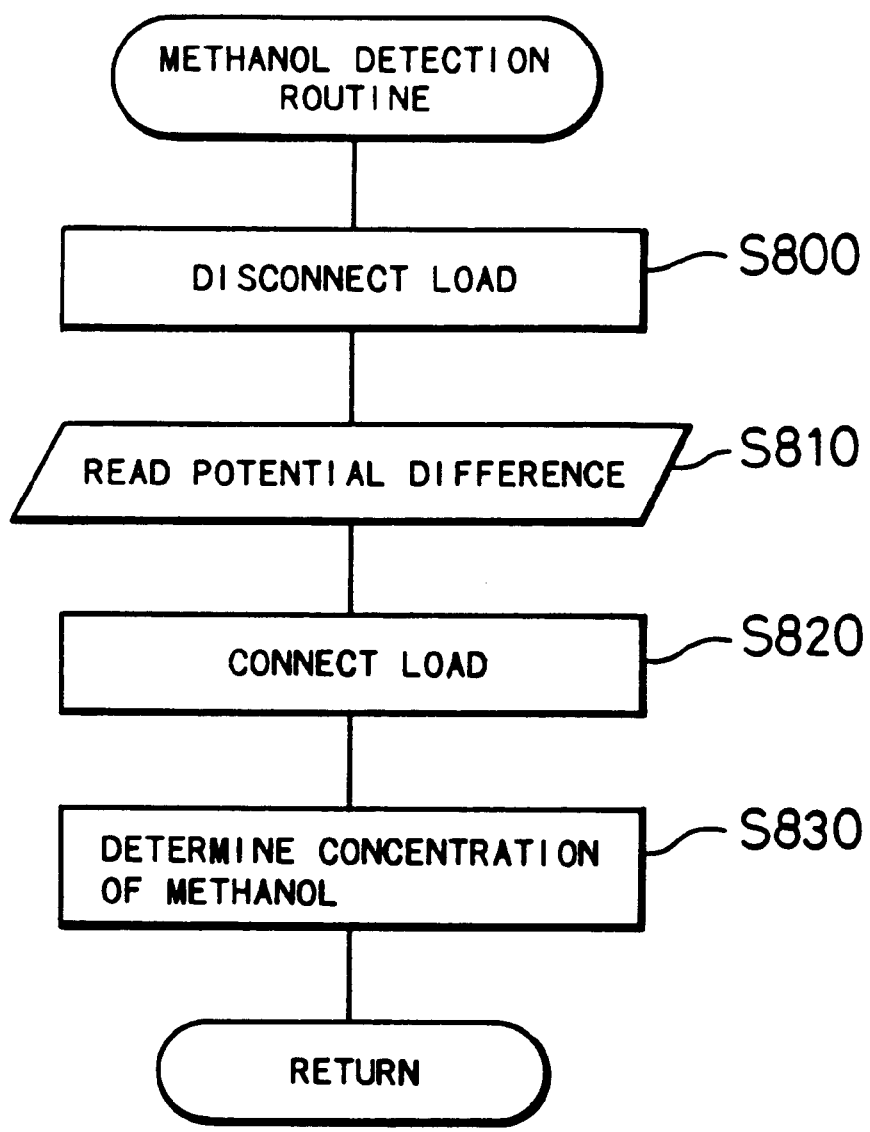
FIG. 20 is a flowchart showing a methanol detection routine executed by the CPU 732 of the electronic control unit 730 in the tenth embodiment.
Figure 21:
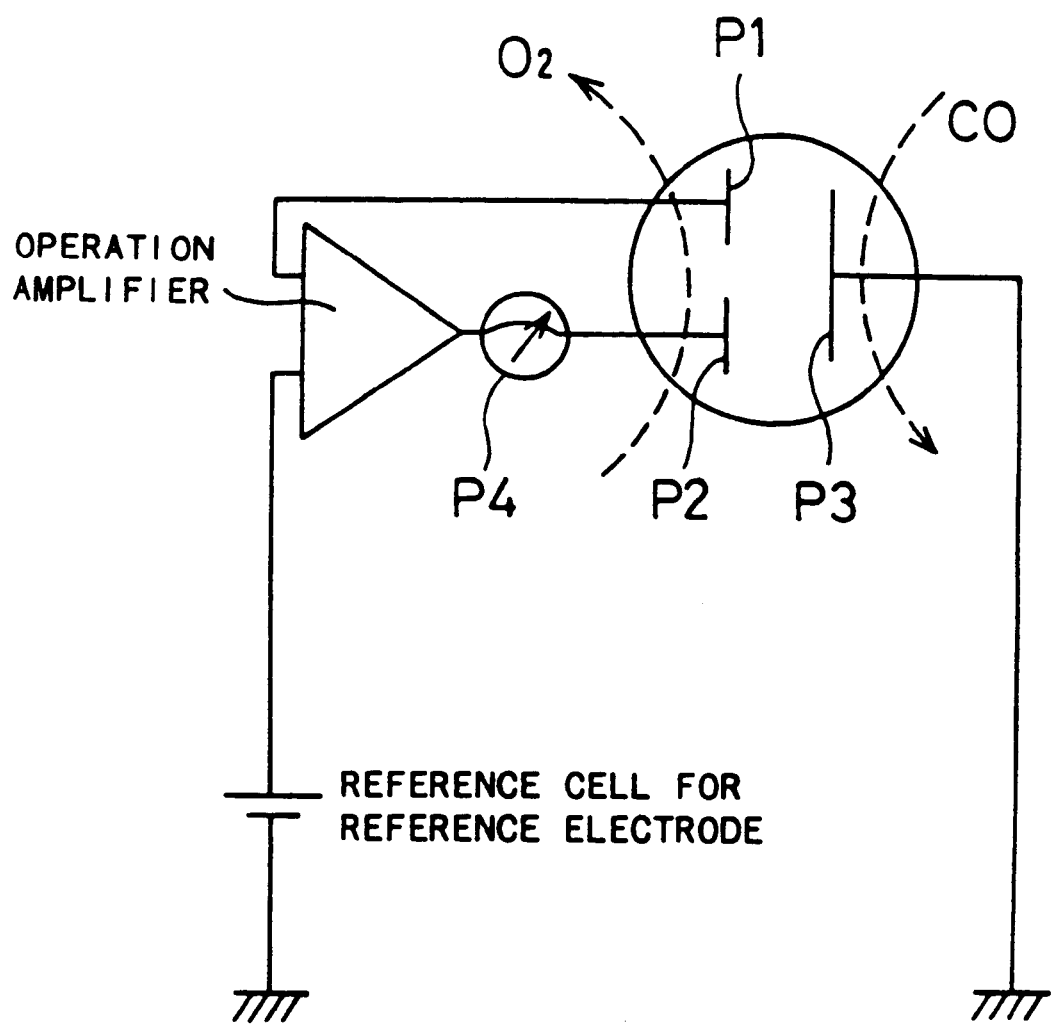
FIG. 21 schematically illustrates structure of a potentiostatic electrolysis-based carbon monoxide sensor as a prior art.

FIG. 20 is a flowchart showing a methanol detection routine executed by the CPU 732 of the electronic control unit 730 in the tenth embodiment. The methanol detection routine is executed as a subroutine of another control routine or at predetermined intervals (for example, at every 100 msec).

When the program enters the methanol detection routine, the CPU 732 first outputs a driving signal via the input/output port 738 to turn on the relay 727 of the cut-off mechanism 726 and open the contact 728 of the relay 727, thereby disconnecting the output terminals 711a and 711b of the stack of fuel cells 710 from the driving apparatus at step S800. The program then proceeds to step S810, at which the CPU 732 reads a potential difference (that is, an open circuit voltage OCV) between the output terminals 711a and 711b of the stack of fuel cells 710 under a no-load condition, as a signal from the voltmeter 724 via the input/output port 738. The CPU 732 then outputs a driving signal to turn off the relay 727 of the cut-off mechanism 726 and close the contact 728 of the relay 727, thereby connecting the output terminals 711a and 711b of the stack of fuel cells 710 with the driving apparatus at step S820. The program subsequently proceeds to step S830, at which the CPU 732 refers to a map previously stored in the ROM 734 and representing a relationship between the concentration of methanol included in the gaseous fuel and the open circuit voltage OCV measured by the voltmeter 724, for example, the map shown in FIG. 13, and determines the concentration of methanol corresponding to the input open circuit voltage OCV. After the determination, the program goes to RETURN and exits from the routine.

The connection of the output terminals 711a and 711b of the stack of fuel cells 710 with the driving apparatus is intercepted for a time period between the execution of step S800 and that of step S820. The time period is varied depending upon the characteristics of the stack of fuel cells 710 and the voltmeter 724, but generally ranges from several to ten-odd milliseconds. Since the driving apparatus has relatively slow response, the temporary, short-time interception does not affect the driving apparatus but allows continuous operation of the driving apparatus.

The concentration of methanol in the gaseous fuel thus determined by the methanol concentration-measuring apparatus 701 as well as the concentration of carbon monoxide in the gaseous fuel determined by the carbon monoxide sensor 719 is used for controlling operations of the reformer 716. Some examples of such control are given below, although the process of control is not described in detail. According to one structure, when the concentration of methanol in the gaseous fuel is not less than a predetermined level (for example, 1%), operation of the reformer 716 is controlled to reduce methanol in the gaseous fuel. For example, the temperature of the reformer unit 716a is increased to enhance the reactivity of methanol. When the concentration of carbon monoxide in the gaseous fuel is not less than a predetermined level (for example, 10 ppm), operation of the reformer 716 is controlled to reduce carbon monoxide in the gaseous fuel. For example, an air flow fed to the partial oxidizing unit 716c is increased.

The methanol concentration-measuring apparatus 701 of the tenth embodiment can determine the concentration of methanol included in the gaseous fuel or object gas with high precision, without adding any specific hardware to the fuel cell generator system 700. This effectively reduces the size of the whole fuel cell generator system 700. The reformer 716 is efficiently driven and controlled according to the results of measurement, that is, the concentration of methanol and the concentration of carbon monoxide.

The sixth through the tenth embodiments described above are related to the apparatus for measuring methanol. This structure of the embodiments is applicable to apparatus for measuring specific organic compounds including methanol. Methanol is an only organic compound which may be detected from the hydrogen-rich gaseous fuel generated by reforming methanol. Organic compounds other than methanol may be detected from hydrogen-rich gas generated by reforming petroleum or the like. The structure of the sixth through the tenth embodiments is applicable for measuring substances satisfying the following three conditions: passing through the electrolyte membrane; causing oxidation on the anode exposed to oxygen after the permeation; and not doing damage, like change of properties or dissolution, to the electrolyte membrane.

Organic compounds detectable by the substantially similar structure to those of the sixth through the tenth embodiments include:

alcohols, such as methanol, ethanol, propanol, butanol, pentanol, octanol, and benzyl alcohol;

ketones, such as acetone, methyl ethyl ketone, methyl propyl ketone, methyl butyl ketone, diethyl ketone, and dipropyl ketone;

amines, such as propylamine;

esters, such as methyl acetate;

ethers, such as diethyl ether; and glycerols, such as ethylene glycol, ethylene glycol ethyl ether, propylene glycol, and glycerol.

In the structure of measuring any one of the above organic compounds, a map representing a relationship between the concentration of the organic compound of interest included in the hydrogen-containing reactant gas and the open circuit voltage OCV measured by the voltmeter (532 or 632) is prepared in advance. The structure determines the concentration of the organic compound of interest, which is included in the hydrogen-containing reactant gas, corresponding to the open circuit voltage OCV by referring to the map.

The structure of the sixth through the tenth embodiments is also applicable for measuring lower alcohols, such as methanol, ethanol, propanol, butanol, and pentanol. These lower alcohols can be detected by substantially the same structure as those of the sixth through the tenth embodiments. A map representing a relationship between the concentration of the lower alcohol of interest included in the hydrogen-containing reactant gas and the open circuit voltage OCV measured by the voltmeter (532 or 632) is prepared in advance. The structure determines the concentration of the lower alcohol of interest, which is included in the hydrogen-containing reactant gas, corresponding to the open circuit voltage OCV by referring to the map.

The above embodiments are only illustrative and not restrictive in any sense. There may be many other modifications, alterations, and changes without departing from the scope or spirit of essential characteristics of the invention. The scope and spirit of the present invention are limited only by the terms of the appended claims.

What is claimed is:

1. An apparatus for detecting an organic compound included in a hydrogen-containing reactant gas, said apparatus comprising:

a sandwich structure comprising an electrolyte membrane and first and second electrodes with a catalyst carried thereon, said first and second electrodes being arranged across said electrolyte membrane;

a reactant gas supply conduit for supplying said reactant gas to said first electrode;

an oxygen gas supply conduit for supplying an oxygen-containing gas to said second electrode;

potential difference measurement means for measuring a potential difference between said first and second electrodes;

an elastic member for pushing up said sandwich structure from the side of said second electrode;

a communicating conduit which communicates with said reactant gas supply conduit and emits said reactant gas to the air; and a valve mechanism which is positioned in said communicating conduit and utilizes said sandwich structure to be pushed up by said elastic member as a valve, said valve mechanism being driven to an open position by overcoming the pressing force applied by said elastic member and moving said valve when a pressure in said reactant gas supply conduit becomes greater than a predetermined level.

2. An apparatus for detecting carbon monoxide included in a hydrogen-containing reactant gas, said apparatus comprising:

an electrolyte membrane;

first and second electrodes with a catalyst carried thereon, said first and second electrodes being arranged across said electrolyte membrane;

a reactant gas supply conduit for supplying said reactant gas to said first electrode;

an oxygen gas supply conduit for supplying an oxygen-containing gas to said second electrode;

a predetermined load connected to said first and second electrodes; and potential difference measurement means for measuring a potential difference between said first and second electrodes;

said apparatus further comprising:

a connection passage for connecting said reactant gas supply conduit to the atmosphere; and valve means disposed in said connection passage, said valve means being driven to an open position when a pressure in said reactant gas supply conduit becomes greater than a predetermined level; and valve state detection means for detecting said valve means in its open position.

3. An apparatus for detecting an organic compound included in a hydrogen-containing reactant gas, said apparatus comprising:

a sandwich structure comprising an electrolyte membrane and first and second electrodes with a catalyst carried thereon, said first and second electrodes being arranged across said electrolyte membrane;

a reactant gas supply conduit for supplying said reactant gas to said first electrode;

an oxygen gas supply conduit for supplying an oxygen-containing gas to said second electrode;

potential difference measurement means for measuring a potential difference between said first and second electrodes;

an elastic member for pushing up said sandwich structure from the side of said second electrode;

a communicating conduit which communicates with said reactant gas supply conduit and emits said reactant gas to the air;

a valve mechanism which is positioned in said communicating conduit and utilizes said sandwich structure to be pushed up by said elastic member as a valve, said valve mechanism being driven to an open position by overcoming the pressure force applied by said elastic member and moving said valve when a pressure in said reactant gas supply conduit becomes greater than a predetermined level; and valve state detection means for detecting said valve means in its open position based on the detection results of said potential difference measurement means.

4. An apparatus in accordance with claim 3, said apparatus further comprising:

temperature control means for controlling temperature of said first electrode.

5. An apparatus in accordance with claim 3, said apparatus further comprising:

switching means for moving between a first position where a predetermined load is connected to said first and second electrodes and a second position where said predetermined load is disconnected from said first and second electrodes;

means for calculating a concentration of carbon monoxide included in said reactant gas, based on the potential difference measured by said potential difference measurement means, while said switching means is in said first position; and means for calculating a concentration of said organic compound included in said reactant gas, based on the potential difference measured by said potential difference measurement means while said switching means is in said second position.

6. An apparatus in accordance with claim 3, said apparatus further comprising:

means for calculating a concentration of said organic compound included in said reactant gas, based on the potential difference measured by said potential difference measurement means.

7. An apparatus in accordance with claim 3, said apparatus further comprising:

determination means for determining that said organic compound of not less than a predetermined concentration exists in said reactant gas when the potential difference measured by said potential difference measurement means is not greater than a preset value.

* * * * *

UNITED STATES PATENT AND TRADEMARK OFFICE
CERTIFICATE OF CORRECTION

PATENT NO. : 5,897,766

DATED : April 27, 1999

INVENTOR(S): Shigeyuki KAWATSU

It is certified that an error appears in the above-identified patent and that said Letters Patent is hereby corrected as shown below:

On the title page, item [73], the assignee's name should be:

--Toyota Jidosha Kabushiki Kaisha--

Signed and Sealed this

Twenty-first Day of March, 2000

*Attest:*

Q. TODD DICKINSON

*Attesting Officer*       *Commissioner of Patents and Trademarks*